(12) United States Patent
Cirillo et al.

(10) Patent No.: US 6,720,321 B2
(45) Date of Patent: Apr. 13, 2004

(54) 1,4-DISUBSTITUTED BENZO-FUSED CYCLOALKYL UREA COMPOUNDS

(75) Inventors: Pier Francesco Cirillo, Woodbury, CT (US); Eugene R. Hickey, Danbury, CT (US)

(73) Assignee: Boehringer Ingelheim Pharmaceuticals, Inc., Ridgefield, CT (US)

(*) Notice: Subject to any disclaimer, the term of this patent is extended or adjusted under 35 U.S.C. 154(b) by 53 days.

(21) Appl. No.: 10/154,535

(22) Filed: May 24, 2002

(65) Prior Publication Data

US 2003/0100608 A1 May 29, 2003

Related U.S. Application Data

(60) Provisional application No. 60/295,909, filed on Jun. 5, 2001.

(51) Int. Cl.[7] .................. A61K 31/5355; C07D 413/06
(52) U.S. Cl. .................... 514/235.8; 514/269; 544/123; 544/319
(58) Field of Search ................ 544/123, 319; 514/235.8, 269

(56) References Cited

U.S. PATENT DOCUMENTS 6,297,381 B1   10/2001   Cirillo et al.
6,319,921 B1   11/2001   Cirillo et al.
6,358,945 B1    3/2002   Breitfelder et al.

FOREIGN PATENT DOCUMENTS

| WO | WO 99/32110 A1 | 7/1999 |
| WO | WO 99/32111 A1 | 7/1999 |
| WO | WO 99/32463 A1 | 7/1999 |
| WO | WO 01/36403 A1 | 11/2000 |

*Primary Examiner*—Joseph K. McKane
*Assistant Examiner*—Kamal Saeed
(74) *Attorney, Agent, or Firm*—Robert P. Raymond; Anthony P. Bottino; Timothy X. Witkowski

(57) ABSTRACT

Disclosed are compounds of the formula (I) shown below which are active as anti-inflammatory agents. Also disclosed are methods of using and making such compounds.

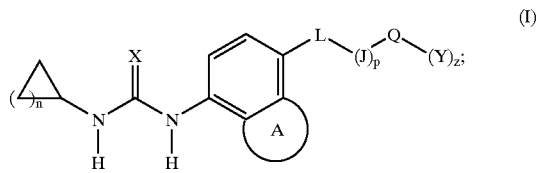

wherein n, X, A, L, J, p, Q, Y and z are described herein.

16 Claims, No Drawings

1,4-DISUBSTITUTED BENZO-FUSED CYCLOALKYL UREA COMPOUNDS

APPLICATION DATA

This application claims benefit to U.S. provisional application No. 60/295,909 filed Jun. 5, 2001.

TECHNICAL FIELD OF THE INVENTION

This invention relates to novel 1,4-disubstituted benzo-fused cycloalkyl urea compounds of formula(I):

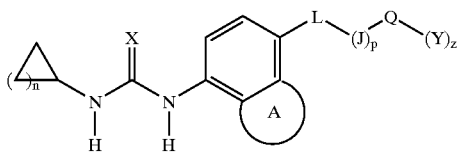

wherein X, A, L, J, Q and Y of formula(I) are defined below. The compounds of the invention inhibit production of cytokines involved in inflammatory processes and are thus useful for treating diseases and pathological conditions involving inflammation such as chronic inflammatory disease. This invention also relates to processes for preparing these compounds and to pharmaceutical compositions comprising these compounds.

BACKGROUND OF THE INVENTION

Tumor necrosis factor (TNF) and interleukin-1 (IL-1) are important biological entities collectively referred to as proinflammatory cytokines. These, along with several other related molecules, mediate the inflammatory response associated with the immunological recognition of infectious agents. The inflammatory response plays an important role in limiting and controlling pathogenic infections.

Elevated levels of proinflammatory cytokines are also associated with a number of diseases of autoimmunity such as toxic shock syndrome, rheumatoid arthritis, osteoarthritis, diabetes and inflammatory bowel disease (Dinarello, C. A., et al., 1984, *Rev. Infect. Disease* 6:51). In these diseases, chronic elevation of inflammation exacerbates or causes much of the pathophysiology observed. For example, rheumatoid synovial tissue becomes invaded with inflammatory cells that result in destruction to cartilage and bone (Koch, A. E., et al., 1995, *J. Invest. Med.* 43: 28–38). Studies suggest that inflammatory changes mediated by cytokines may be involved in the pathogenesis of restenosis after percutaneous transluminal coronary angioplasty (PTCA) (Tashiro, H., et al., 2001 March, *Coron Artery Dis* 12(2): 107–13). An important and accepted therapeutic approach for potential drug intervention in these diseases is the reduction of proinflammatory cytokines such as TNF (also referred to in its secreted cell-free form as TNFα) and IL-1β. A number of anti-cytokine therapies are currently in clinical trials. Efficacy has been demonstrated with a monoclonal antibody directed against TNFα in a number of autoimmune diseases (Heath, P., "CDP571: An Engineered Human IgG4 Anti-TNFα Antibody" IBC Meeting on Cytokine Antagonists, Philadelphia, Pa., Apr. 24–5, 1997). These include the treatment of rheumatoid arthritis, Crohn's disease and ulcerative colitis (Rankin, E. C. C., et al., 1997, *British J. Rheum.* 35: 334–342 and Stack, W. A., et al., 1997, *Lancet* 349: 521–524). The monoclonal antibody is thought to function by binding to both soluble TNFα and to membrane bound TNF.

A soluble TNFα receptor has been engineered that interacts with TNFα. The approach is similar to that described above for the monoclonal antibodies directed against TNFα; both agents bind to soluble TNFα, thus reducing its concentration. One version of this construct, called Enbrel (Immunex, Seattle, Wash.) recently demonstrated efficacy in a Phase III clinical trial for the treatment of rheumatoid arthritis (Brower et al., 1997, *Nature Biotechnology* 15: 1240). Another version of the TNFα receptor, Ro 45-2081 (Hoffman-LaRoche Inc., Nutley, N.J.) has demonstrated efficacy in various animal models of allergic lung inflammation and acute lung injury. Ro 45-2081 is a recombinant chimeric molecule constructed from the soluble 55 kDa human TNF receptor fused to the hinge region of the heavy chain IgG1 gene and expressed in eukaryotic cells (Renzetti, et al., 1997, *Inflamm. Res.* 46: S143).

IL-1 has been implicated as an immunological effector molecule in a large number of disease processes. IL-1 receptor antagonist (IL-1ra) had been examined in human clinical trials. Efficacy has been demonstrated for the treatment of rheumatoid arthritis (Antril, Amgen). In a phase III human clinical trial IL-1ra reduced the mortality rate in patients with septic shock syndrome (Dinarello, 1995, *Nutrution* 11, 492). Osteoarthritis is a slow progressive disease characterized by destruction of the articular cartilage. IL-1 is detected in synovial fluid and in the cartilage matrix of osteoarthritic joints. Antagonists of IL-1 have been shown to diminish the degradation of cartilage matrix components in a variety of experimental models of arthritis (Chevalier, 1997, *Biomed Pharmacother.* 51, 58). Nitric oxide (NO) is a mediator of cardiovascular homeostasis, neurotransmission and immune function; recently it has been shown to have important effects in the modulation of bone remodeling. Cytokines such as IL-1 and TNF are potent stimulators of NO production. NO is an important regulatory molecule in bone with effects on cells of the osteoblast and osteoclast lineage (Evans, et al., 1996, *J Bone Miner Res.* 11, 300). The promotion of beta-cell destruction leading to insulin dependent diabetes mellitus shows dependence on IL-1. Some of this damage may be mediated through other effectors such as prostaglandins and thromboxanes. IL-1 can effect this process by controlling the level of both cyclooxygenase II and inducible nitric oxide synthetase expression (McDaniel et al., 1996, *Proc Soc Exp Biol Med.* 211, 24).

Inhibitors of cytokine production are expected to block inducible cyclooxygenase (COX-2) expression. COX-2 expression has been shown to be increased by cytokines and it is believed to be the isoform of cyclooxygenase responsible for inflammation (M. K. O'Banion et al., *Proc. Natl. Acad. Sci. U.S.A*, 1992, 89, 4888.) Accordingly, inhibitors of cytokines such as IL-1 would be expected to exhibit efficacy against those disorders currently treated with COX inhibitors such as the familiar NSAIDs. These disorders include acute and chronic pain as well as symptoms of inflammation and cardiovascular disease.

Elevation of several cytokines have been demonstrated during active inflammatory bowel disease (IBD). A mucosal imbalance of intestinal IL-1 and IL-1ra is present in patients with IBD. Insufficient production of endogenous IL-1ra may contribute to the pathogenesis of IBD (Cominelli, et al., 1996, *Aliment Pharmacol Ther.* 10, 49). Alzheimer disease is characterized by the presence of beta-amyloid protein deposits, neurofibrillary tangles and cholinergic dysfunction throughout the hippocampal region. The structural and metabolic damage found in Alzheimer disease is possibly due to a sustained elevation of IL-1 (Holden, et al., 1995,

*Med Hypotheses*, 45, 559). A role for IL-1 in the pathogenesis of human immunodeficiency virus (HIV) has been identified. IL-1ra showed a clear relationship to acute inflammatory events as well as to the different disease stages in the pathophysiology of HIV infection (Kreuzero, et al., 1997, *Clin Exp Immunol.* 109, 54). IL-1 and TNF are both involved in periodontal disease. The destructive process associated with periodontal disease may be due to a disregulation of both IL-1 and TNF (Howells, 1995, *Oral Dis.* 1, 266).

Proinflammatory cytokines such as TNFα and IL-1β a are also important mediators of septic shock and associated cardiopulmonary dysfunction, acute respiratory distress syndrome (ARDS) and multiple organ failure. In a study of patients presenting at a hospital with sepsis, a correlation was found between TNFα and IL-6 levels and septic complications (Terregino et al., 2000, *Ann. Emerg. Med.*, 35, 26). TNFα has also been implicated in cachexia and muscle degradation, associated with HIV infection (Lahdiverta et al., 1988, *Amer. J. Med.*, 85, 289). Obesity is associated with an increase incidence of infection, diabetes and cardiovascular disease. Abnormalities in TNFα expression have been noted for each of the above conditions (Loffreda, et al., 1998, *FASEB J.* 12, 57). It has been proposed that elevated levels of TNFα are involved in other eating related disorders such as anorexia and bulimia nervosa. Pathophysiological parallels are drawn between anorexia nervosa and cancer cachexia (Holden, et al., 1996, *Med Hypotheses* 47, 423). An inhibitor of TNFα production, HU-211, was shown to improve the outcome of closed brain injury in an experimental model (Shohami, et al., 1997, *J Neuroimmunol.* 72, 169). Atherosclerosis is known to have an inflammatory component and cytokines such as IL-1 and TNF have been suggested to promote the disease. In an animal model an IL-1 receptor antagonist was shown to inhibit fatty streak formation (Elhage et al., 1998, *Circulation*, 97, 242).

TNFα levels are elevated in airways of patients with chronic obstructive pulmonary disease and it may contribute to the pathogenesis of this disease (M. A. Higham et al., 2000, *Eur. Respiratory J.*, 15, 281). Circulating TNFα may also contribute to weight loss associated with this disease (N. Takabatake et al., 2000, *Amer. J. Resp. & Crit. Care Med.*,161 (4 Pt 1), 1179). Elevated TNFα levels have also been found to be associated with congestive heart failure and the level has been correlated with severity of the disease (A. M. Feldman et al., 2000, *J. Amer. College of Cardiology*, 35, 537). In addition, TNFα has been implicated in reperfusion injury in lung (Borjesson et al., 2000, *Amer. J. Physiol.*, 278, L3–12), kidney (Lemay et al., 2000, *Transplantation*, 69, 959), and the nervous system (Mitsui et al., 1999, *Brain Res.*, 844, 192).

TNFα is also a potent osteoclastogenic agent and is involved in bone resorption and diseases involving bone resorption (Abu-Amer et al., 2000, *J. Biol. Chem.*, 275, 27307). It has also been found highly expressed in chondrocytes of patients with traumatic arthritis (Melchiorri et al., 2000, *Arthritis and Rheumatism*, 41, 2165). TNFα has also been shown to play a key role in the development of glomerulonephritis (Le Hir et al., 1998, *Laboratory Investigation*, 78, 1625).

The abnormal expression of inducible nitric oxide synthetase (iNOS) has been associated with hypertension in the spontaneously hypertensive rat (Chou et al., 1998, *Hypertension*, 31, 643). IL-1 has a role in the expression of iNOS and therefore may also have a role in the pathogenesis of hypertension (Singh et al., 1996, *Amer. J. Hypertension*, 9, 867).

IL-1 has also been shown to induce uveitis in rats which could be inhibited with IL-1 blockers. (Xuan et al., 1998, *J. Ocular Pharmacol. and Ther.*, 14, 31). Cytokines including IL-1, TNF and GM-CSF have been shown to stimulate proliferation of acute myclogenous leukemia blasts (Bruserud, 1996, *Leukemia Res.* 20, 65). IL-1 was shown to be essential for the development of both irritant and allergic contact dermatitis. Epicutaneous sensitization can be prevented by the administration of an anti-IL-1 monoclonal antibody before epicutaneous application of an allergen (Muller, et al., 1996, *Am J Contact Dermat.* 7, 177). Data obtained from IL-1 knock out mice indicates the critical involvement in fever for this cytokine (Kluger et al., 1998, *Clin Exp Pharmacol Physiol.* 25, 141). A variety of cytokines including TNF, IL-1, IL-6 and IL-8 initiate the acute-phase reaction which is stereotyped in fever, malaise, myalgia, headaches, cellular hypermetabolism and multiple endocrine and enzyme responses (Beisel, 1995, *Am J Clin Nutr.* 62, 813). The production of these inflammatory cytokines rapidly follows trauma or pathogenic organism invasion.

Other proinflammatory cytokines have been correlated with a variety of disease states. IL-8 correlates with influx of neutrophils into sites of inflammation or injury. Blocking antibodies against IL-8 have demonstrated a role for IL-8 in the neutrophil associated tissue injury in acute inflammation (Harada et al., 1996, *Molecular Medicine Today* 2, 482). Therefore, an inhibitor of IL-8 production may be useful in the treatment of diseases mediated predominantly by neutrophils such as stroke and myocardial infarction, alone or following thrombolytic therapy, thermal injury, adult respiratory distress syndrome (ARDS), multiple organ injury secondary to trauma, acute glomerulonephritis, dermatoses with acute inflammatory components, acute purulent meningitis or other central nervous system disorders, hemodialysis, leukopherisis, granulocyte transfusion associated syndromes, and necrotizing enterocolitis.

Rhinovirus triggers the production of various proinflammatory cytokines, predominantly IL-8, which results in symptomatic illnesses such as acute rhinitis (Winther et al., 1998, *Am J Rhinol.* 12, 17).

Other diseases that are effected by IL-8 include myocardial ischemia and reperfusion, inflammatory bowel disease and many others.

The proinflammatory cytokine IL-6 has been implicated with the acute phase response. IL-6 is a growth factor in a number in oncological diseases including multiple mycloma and related plasma cell dyscrasias (Treon, et al., 1998, *Current Opinion in Hematology* 5: 42). It has also been shown to be an important mediator of inflammation within the central nervous system. Elevated levels of IL-6 are found in several neurological disorders including AIDS dementia complex, Alzheimer's disease, multiple sclerosis, systemic lupus erythematosus, CNS trauma and viral and bacterial meningitis (Gruol, et al., 1997, *Molecular Neurobiology* 15: 307). IL-6 also plays a significant role in osteoporosis. In murine models it has been shown to effect bone resorption and to induce osteoclast activity (Ershler et al., 1997, *Development and Comparative Immunol.* 21: 487). Marked cytokine differences, such as IL-6 levels, exist in vivo between osteoclasts of normal bone and bone from patients with Paget's disease (Mills, et al., 1997, *Calcif Tissue Int.* 61, 16). A number of cytokines have been shown to be involved in cancer cachexia. The severity of key parameters of cachexia can be reduced by treatment with anti IL-6 antibodies or with IL-6 receptor antagonists (Strassmann, et al., 1995, *Cytokins Mol Ther.* 1, 107). Several infectious diseases, such as influenza, indicate IL-6 and IFN alpha as key factors in both symptom formation and in host defense (Hayden, et al., 1998, *J Clin Invest*. 101, 643). Overexpression of IL-6 has been implicated in the pathology of a number of diseases including multiple myeloma, rheumatoid arthritis, Castleman's disease, psoriasis and postmenopausal osteoporosis (Simpson, et al., 1997, *Protein Sci*. 6, 929). Compounds that interfered with the production of cytokines including IL-6, and TNF were effective in blocking a passive cutaneous anaphylaxis in mice (Scholz et al., 1998, *J. Med. Chem.*, 41, 1050).

GM-CSF is another proinflammatory cytokine with relevance to a number of therapeutic diseases. It influences not only proliferation and differentiation of stem cells but also regulates several other cells involved in acute and chronic inflammation. Treatment with GM-CSF has been attempted in a number of disease states including burn-wound healing, skin-graft resolution as well as cytostatic and radiotherapy induced mucositis (Masucci, 1996, *Medical Oncology* 13: 149). GM-CSF also appears to play a role in the replication of human immunodeficiency virus (HIV) in cells of macrophage lineage with relevance to AIDS therapy (Crowe et al., 1997, *Journal of Leukocyte Biology* 62, 41). Bronchial asthma is characterised by an inflammatory process in lungs. Involved cytokines include GM-CSF amongst others (Lee, 1998, *J R Coll Physicians Lond* 32, 56).

Interferon γ (IFN γ) has been implicated in a number of diseases. It has been associated with increased collagen deposition that is a central histopathological feature of graft-versus-host disease (Parkman, 1998, *Curr Opin Hematol*. 5, 22). Following kidney transplantation, a patient was diagnosed with acute myelogenous leukemia. Retrospective analysis of peripheral blood cytokines revealed elevated levels of GM-CSF and IFN γ. These elevated levels coincided with a rise in peripheral blood white cell count (Burke, et al., 1995, *Leuk Lymphoma*. 19, 173). The development of insulin-dependent diabetes (Type 1) can be correlated with the accumulation in pancreatic islet cells of T-cells producing IFN γ (Ablumunits, et al., 1998, *J Autoimmun*. 11, 73). IFN γ along with TNF, IL-2 and IL-6 lead to the activation of most peripheral T-cells prior to the development of lesions in the central nervous system for diseases such as multiple sclerosis (MS) and AIDS dementia complex (Martino et al., 1998, *Ann Neurol*. 43, 340). Atherosclerotic lesions result in arterial disease that can lead to cardiac and cerebral infarction. Many activated immune cells are present in these lesions, mainly T-cells and macrophages. These cells produce large amounts of proinflammatory cytokines such as TNF, IL-1 and IFN γ. These cytokines are thought to be involved in promoting apoptosis or programmed cell death of the surrounding vascular smooth muscle cells resulting in the atherosclerotic lesions (Geng, 1997, *Heart Vessels Suppl* 12, 76). Allergic subjects produce mRNA specific for IFN γ following challenge with Vespula venom (Bonay, et al., 1997, *Clin Exp Immunol*. 109, 342). The expression of a number of cytokines, including IFN γ has been shown to increase following a delayed type hypersensitivity reaction thus indicating a role for IFN γ in atopic dermatitis (Szepietowski, et al., 1997, *Br J Dermatol*. 137, 195). Histopathologic and immunohistologic studies were performed in cases of fatal cerebral malaria. Evidence for elevated IFN γ amongst other cytokines was observed indicating a role in this disease (Udomsangpetch et al., 1997, *Am J Trop Med Hyg*. 57, 501). The importance of free radical species in the pathogenesis of various infectious diseases has been established. The nitric oxide synthesis pathway is activated in response to infection with certain viruses via the induction of proinflammatory cytokines such as IFN γ (Akaike, et al., 1998, *Proc Soc Exp Biol Med*. 217, 64). Patients, chronically infected with hepatitis B virus (HBV) can develop cirrhosis and hepatocellular carcinoma. Viral gene expression and replication in HBV transgenic mice can be suppressed by a post-transcriptional mechanism mediated by IFN γ, TNF and IL-2 (Chisari, et al., 1995, *Springer Semin Immunopathol*. 17, 261). IFN γ can selectively inhibit cytokine induced bone resorption. It appears to do this via the intermediacy of nitric oxide (NO) which is an important regulatory molecule in bone remodeling. NO may be involved as a mediator of bone disease for such diseases as: the rheumatoid arthritis, tumor associated osteolysis and postmenopausal osteoporosis (Evans, et al., 1996, *J Bone Miner Res*. 11, 300). Studies with gene deficient mice have demonstrated that the IL-12 dependent production of IFN γ is critical in the control of early parasitic growth. Although this process is independent of nitric oxide the control of chronic infection does appear to be NO dependent (Alexander et al., 1997, *Philos Trans R Soc Lond B Biol Sci* 352, 1355). NO is an important vasodilator and convincing evidence exists for its role in cardiovascular shock (Kilbourn, et al., 1997, *Dis Mon*. 43, 277). IFN γ is required for progression of chronic intestinal inflammation in such diseases as Crohn's disease and inflammatory bowel disease (IBD) presumably through the intermediacy of CD4+ lymphocytes probably of the TH 1 phenotype (Sartor 1996, *Aliment Pharmacol Ther*. 10 Suppl 2, 43). An elevated level of serum IgE is associated with various atopic diseases such as bronchial asthma and atopic dermatitis. The level of IFN γ was negatively correlated with serum IgE suggesting a role for IFN γ in atopic patients (Teramoto et al., 1998, *Clin Exp Allergy* 28, 74).

WO 01/01986 discloses particular compounds alleged to having the ability to inhibit TNFα. The specific inhibitors disclosed are structurally distinct from the novel compounds disclosed in the present application disclosed hereinbelow. Certain compounds disclosed in WO 01/01986 are indicated to be effective in treating the following diseases: dementia associated with HIV infection, glaucoma, optic-neuropathy, optic neuritis, retinal ischemia, laser induced optic damage, surgery or trauma-induced proliferative vitreoretinopathy, cerebral ischemia, hypoxia-ischemia, hypoglycemia, domoic acid poisoning, anoxia, carbon monoxide or manganese or cyanide poisoning, Huntington's disease, Alzheimer's disease, Parkinson's disease, meningitis, multiple sclerosis and other demyelinating diseases, amyotrophic lateral sclerosis, head and spinal cord trauma, seizures, convulsions, olivopontocerebellar atrophy, neuropathic pain syndromes, diabetic neuropathy, HIV-related neuropathy, MERRF and MELAS syndromes, Leber's disease, Wernicke's encephalophathy, Rett syndrome, homocysteinuria, hyperprolinemia, hyperhomocysteinemia, nonketotic hyperglycinemia, hydroxybutyric aminoaciduria, sulfite oxidase deficiency, combined systems disease, lead encephalopathy, Tourett's syndrome, hepatic encephalopathy, drug addiction, drug tolerance, drug dependency, depression, anxiety and schizophrenia. WO 02/32862 discloses that inhibitors of pro-inflammatory cytokines including TNFα are allegedly useful for treating acute and chronic inflammation in the lung caused by inhalation of smoke such as cigarette smoke.

Compounds which modulate release of one or more of the aforementioned inflammatory cytokines can be useful in treating diseases associated with release of these cytokines. For example, WO 98/52558 discloses heteroaryl urea compounds which are indicated to be useful in treating cytokine mediated diseases. WO 99/23091 discloses another class of urea compounds which are useful as anti-inflammatory agents. WO 99/32463 relates to aryl ureas amd their use in treating cytokine diseases and proteolytic enzyme mediated disease. WO 00/41698 discloses aryl ureas said to be useful in treating p38 MAP kinase diseases.

U.S. Pat. No. 5,162,360 discloses N-substituted aryl-N'-heterocyclic substituted urea compounds which are described as being useful for treating hypercholesterolemia and atheroclerosis.

The work cited above supports the principle that inhibition of cytokine production will be beneficial in the treatment of various disease states. Some protein therapeutics are in late development or have been approved for use in particular diseases. Protein therapeutics are costly to produce and have bioavailability and stability problems. Therefore a need exists for new small molecule inhibitors of cytokine production with optimized efficacy, pharmacokinetic and safety profiles.

BRIEF SUMMARY OF THE INVENTION

The work cited above supports the principle that inhibition of cytokine production will be beneficial in the treatment of various disease states.

It is therefore an object of the invention to provide novel compounds which inhibit the release of inflammatory cytokines such as interleukin-1 and tumor necrosis factor.

It is a further object of the invention to provide methods for treating diseases and pathological conditions involving inflammation such as chronic inflammatory disease, using the novel compounds of the invention.

It is yet a further object of the invention to provide processes of preparation of the above-mentioned novel compounds.

DETAILED DESCRIPTION OF THE INVENTION

In the broadest generic aspect of the invention, there are provided compounds of the formula (I):

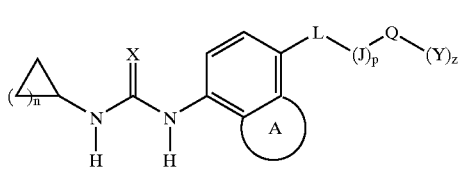

wherein:
n is 1, 2, 3, 4 or 5 such that the cycloalkyl group is chosen from cyclopropyl, cyclobutyl, cyclopentyl, cyclohexyl and cycloheptyl, each optionally independently substituted by one to two $R_1$ or $R_2$;
X is O;
p is 0 or 1;
z is 0 or 1;
m is 0, 1 or 2;
ring A is:
fused saturated or unsaturated ring containing 3–5 carbon atoms wherein ring A or the phenyl ring to which it is fused is optionally substituted by one or more $C_{1-6}$ branched or unbranched alkyl optionally partially or fully halogenated, acetyl, aroyl, $C_{1-6}$ branched or unbranched alkoxy optionally partially or fully halogenated, halogen, methoxycarbonyl, phenylsulfonyl, hydroxy, amino, mono- or di-($C_{1-4}$ alkyl)amino, mono- or di-($C_{1-4}$ alkyl)amino-S(O)$_2$, cyano, nitro or $H_2NSO_2$;

Preferred formula (I) compounds are those where ring A and the phenyl ring to which it is fused form:

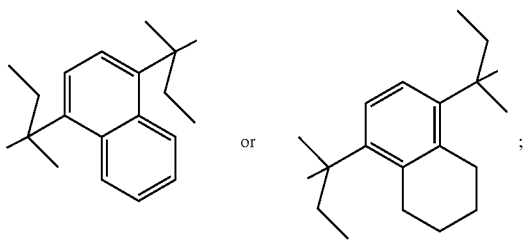

L is:
(i) a bond or an acyclic group chosen from: —O—; —NH—; >C(O); >C(S);
$C_{1-10}$ saturated or unsaturated branched or unbranched carbon chain;
wherein one or more carbon atoms are optionally independently replaced by heteroatoms chosen from O, N and S(O)$_m$; and
wherein said acyclic group is optionally substituted with 0–2 oxo groups, one or more $C_{1-4}$ branched or unbranched alkyl optionally substituted by one or more halogen atoms, hydroxy, amino or imino;
or L is
(ii) a cyclic group chosen from: a $C_{5-8}$ cycloalkyl or cycloalkenyl optionally substituted with one to two oxo groups or one to three $C_{1-4}$ alkyl, $C_{11-4}$ alkoxy or $C_{1-4}$ alkylamino chains each being branched or unbranched;
aryl, furanyl, thienyl, pyrrolyl, pyrazolyl, imidazolyl, pyridinyl, pyrimidinyl, pyridinonyl, dihydropyridinonyl, piperdinyl, benzimidazole, piperazinyl, pyridazinyl or pyrazinyl; each being optionally independently substituted with one to three $C_{1-4}$ alkyl, $C_{1-4}$alkoxy, oxo, hydroxy, nitrile, amino, mono- or di-($C_{1-3}$ alkyl)amino, mono- or di-($C_{1-3}$ alkylamino)carbonyl, NH$_2$C(O), $C_{1-6}$ alkyl-S(O)$_m$ or halogen;
with the proviso that:
when L is (i), then p is 0;
and when L is (ii), then z is 0;
J is chosen from —CH$_2$—, —CH$_2$CH$_2$—, —CH$_2$CH(CH$_3$)—, —CH$_2$CH(OH)—, —CH(OH)— and >C(O);
Q is
phenyl, naphthyl, pyridinyl, pyrimidinyl, pyridazinyl, imidazolyl, benzimidazolyl, furanyl, thienyl, pyranyl, thiazolyl, oxazolyl, naphthyridinyl, pyrazinyl, pyrazolyl, triazolyl, tetrazolyl, pyrazolo[3,4-b]pyrimidinyl, purinyl, pyrrolo[2,3-b]pyridinyl, pyrazolo[3,4-b]pyridinyl, tubercidinyl, oxazo[4,5-b]pyridinyl, 2-oxa-5-aza-bicyclo[2.2.1]heptanyl, 2-thia-5-aza-bicyclo[2.2.1]heptanyl, imidazo[4,5-b]pyridinyl, 1-oxo-λ4-thiomorpholinyl or 13-oxa-11-aza-tricyclo[7.3.1.0-2,7]trideca-2,4,6-triene tetrahydropyranyl, 2-oxo-2H-pyranyl, tetrahydrofuranyl, 1,3-dioxolanone, 1,3-dioxanone, 1,4-dioxanyl, morpholinyl, thiomorpholinyl, 8-oxa-3-aza-bicyclo[3.2.1]octanyl, thiomorpholinyl sulfoxide, thiomorpholinyl sulfone, piperazinyl, piperidinyl, piperidinonyl, tetrahydropyrimidonyl, cyclohexanone, cyclohexanol, pentamethylene sulfide, pentamethylene sulfoxide, pentamethylene sulfone, tetramethylene sulfide, tetramethylene sulfoxide or tetramethylene sulfone each optionally substituted with one to three oxo, $C_{1-6}$ alkyl, phenyl, $C_{1-6}$ alkoxy or hydroxy;

or Q is $C_{1-6}$ alkoxy, secondary or tertiary amine wherein the amino nitrogen is covalently bonded to $C_{1-3}$ alkyl or $C_{1-5}$ alkoxyalkyl, phenylamino, wherein the phenyl ring is optionally substituted with one to two halogen, $C_{1-6}$ alkoxy, hydroxy or mono- or di-($C_{1-3}$ alkyl)amino, $C_{1-6}$ alkyl-S(O)$_m$ or phenyl-S(O)$_m$ wherein the phenyl ring is optionally substituted with one to two halogen, $C_{1-6}$ alkoxy, hydroxy or mono- or di-($C_{1-3}$ alkyl)amino;

$R_1$ is phenyl, benzyl, naphthyl, morpholino, pyridinyl, pyrimidinyl, pyrazinyl, pyridazinyl, pyrrolyl, pyrrolidinyl, piperidinyl, imidazolyl, pyrazolyl, thiazolyl, oxazoyl, [1,3,4]oxadiazol, triazolyl, tetrazolyl, thienyl, furanyl, tetrahydrofuranyl, tetrahydropyranyl, isoxazolyl, isothiazolyl, quinolinyl, isoquinolinyl, indolyl, benzimidazolyl, benzofuranyl, benzoxazolyl, benzisoxazolyl, benzpyrazolyl, benzothiofuranyl, cinnolinyl, pterindinyl, phthalazinyl, naphthypyridinyl, quinoxalinyl, quinazolinyl, purinyl or indazolyl, each of the aforementioned is optionally substituted with one to three phenyl, naphthyl, heterocycle or heteroaryl as hereinabove described in this paragraph, $C_{1-6}$ branched or unbranched alkyl which is optionally partially or fully halogenated, $C_{3-7}$ cycloalkyl$C_{0-2}$ alkyl, bicyclopentanyl, bicyclohexanyl, bicycloheptanyl, phenyl $C_{1-5}$ alkyl, naphthyl $C_{1-5}$ alkyl, halogen, hydroxy, oxo, nitrile, $C_{1-3}$ alkoxy optionally partially or fully halogenated, phenyloxy, naphthyloxy, heteroaryloxy or heterocyclicoxy wherein the heterocyclic or heteroaryl moiety is as hereinabove described in this paragraph, nitro, amino, mono- or di-($C_{1-3}$alky)lamino, phenylamino, naphthylamino, heteroaryl or heterocyclic amino wherein the heteroaryl heterocyclic moiety is as hereinabove described in this paragraph, $NH_2C(O)$, a mono- or di-($C_{1-3}$alkyl)aminocarbonyl, $C_{1-5}$ alkyl-C(O)—$C_{1-4}$ alkyl, amino-$C_{1-5}$ alkyl, mono- or di-($C_{1-5}$alkyl)amino, mono- or di-($C_{1-3}$ alkyl)amino-$C_{1-5}$ alkyl, $C_{1-5}$ alkyl-S(O)$_m$, amino-S(O)$_m$, di-($C_{1-3}$alkyl)amino-S(O)$_m$, $R_3$—$C_{1-5}$alkyl, $R_3$—$C_{1-5}$ alkoxy, $R_3C(O)$—$C_{1-5}$ alkyl, $R_3$—$C_{1-5}$ alkyl($R_4$)N, $C_{1-6}$ acyl, $C_{1-6}$ alkoxy$C_{1-3}$ acyl, carboxy-mono- or di-($C_{1-5}$ alkyl)-amino;

$C_{3-7}$ cycloalkyl$C_{0-5}$ alkyl, bicyclopentanyl, bicyclohexanyl or bicycloheptanyl, each being optionally be partially or fully halogenated and optionally substituted with one to three $C_{1-3}$ alkyl groups;

cyclopentenyl, cyclohexenyl, cycloheptenyl, cyclohexadienyl, cycloheptadienyl, bicyclohexenyl or bicycloheptenyl, each optionally substituted with one to three $C_{1-3}$ alkyl groups;

$C_{1-4}$ alkyl-phenyl-C(O)—$C_{1-4}$ alkyl-, $C_{1-4}$ alkyl-C(O)—$C_{1-4}$ alkyl- or $C_{1-4}$ alkyl-phenyl-S(O)$_m$—$C_{1-4}$ alkyl-;

$C_{1-6}$ alkyl or $C_{1-6}$ alkoxy each of which is branched or unbranched and optionally partially or fully halogenated or optionally substituted with $R_3$;

$R_2$, is a $C_{1-6}$ branched or unbranched alkyl optionally partially or fully halogenated, $C_6$acyl, aroyl, $C_{1-4}$ branched or unbranched alkoxy, each being optionally partially or fully halogenated, carboxy, nitrile, nitro, halogen, $C_{1-6}$ alkoxycarbonyl, $C_{1-6}$ alkyl-S(O)$_m$ optionally partially or fully halogenated, phenyl-S(O)$_m$, amino or aminocarbonyl wherein the N atom is optionally mono-or-disubstituted by $C_{1-6}$ branched or unbranched alkyl, $C_{1-6}$acyl, phenyl or benzyl;

each $R_3$ is independently:
nitrile, $C_{3-7}$ cycloalkyl, phenyl or $NR_5R_6$;

each $R_4$ is independently:
hydrogen or $C_{1-4}$ alkyl optionally partially or fully halogenated;

Y, if present, is covalently attached to Q, and is
a bond, —O—, >C(O), —NH—, —C(O)—NH—, —S—, $C_{1-5}$ alkyl branched or unbranched, $C_{1-3}$ alkyl(OH), $C_{2-5}$ alkenyl, $C_{1-3}$ acyl, heterocycle selected from morpholinyl, piperazinyl, piperidinyl, pyrrolidinyl or tetrahydrofuryl, heteroaryl selected from pyridinyl, pyrimidinyl, pyrazinyl, pyridazinyl, pyrrolyl, imidazolyl, pyrazolyl, thienyl, furyl, isoxazolyl, thiazolyl, oxazolyl, triazolyl, tetrazolyl, isothiazolyl, quinolinyl, isoquinolinyl, indolyl, benzimidazolyl, benzofuranyl, benzoxazolyl, benzisoxazolyl, benzopyrazolyl, benzothiofuranyl, quinoxalinyl, quinazolinyl or indazolyl or aryl each alkyl, alkenyl, acyl, heterocycle, heteroaryl and aryl are optionally substituted by one to three hydroxy, oxo, $C_{1-4}$ alkyl, $C_{1-3}$ alkoxy, $C_{1-4}$ acyl, $C_{1-5}$ alkoxycarbonyl, $NR_5R_6$ or $NR_5R_6$—C(O)—;

wherein each Y is optionally further covalently attached to $NR_5R_6$, $C_{1-4}$ alkyl, $C_{3-7}$ cycloalkyl$C_{0-4}$ alkyl, $C_{1-4}$ alkoxy, aryloxy, hydroxy, aryl$C_{0-4}$ alkyl, heteroaryl$C_{0-4}$ alkyl or heterocycle$C_{0-4}$ alkyl as wherein the heteroaryl and heterocycle moieties are as hereinabove described for Y and the heterocycle, heteroaryl and aryl moieties are optionally substituted by one to three hydroxy, oxo, $C_{1-3}$ alkyl, $C_{1-3}$ alkoxy, $C_{1-5}$ alkoxycarbonyl, $NR_5R_6$ or $NR_5R_6$—C(O)—;

each $R_5$ and $R_6$ are independently hydrogen, $C_{3-7}$ cycloalkyl$C_{0-4}$ alkyl, aryl$C_{0-3}$ alkyl optionally subtituted by halogen, $C_{1-3}$ alkyl or di$C_{1-5}$ alkyl amino, or $R_5$ and $R_6$ are $C_{1-3}$ acyl, aroyl or $C_{1-6}$ branched or unbranched alkyl optionally substituted by $C_{1-5}$ alkoxy, hydroxy, mono- or di-$C_{1-3}$alkylaminocarbonyl or mono or di$C_{1-3}$ alkyl amino wherein said $C_{1-6}$ alkyl optionally partially or fully halogenated;

or $R_5$ and $R_6$ taken together optionally form a heteroring chosen from morpholinyl, morpholino, thiomorpholino, piperidinyl, pyridazinyl, pyrimidinyl, imidazolyl, pyridinyl, tetrazolyl, thiazolyl, oxazolyl, pyrazolyl, pyrrolyl and pyrrolidinyl;

and the pharmaceutically acceptable derivatives thereof.

In a first subgeneric aspect of the invention, there are provided compounds of the formula (I) as described in the broadest generic aspect above and wherein:

L is (i);

z is 0 or 1;

n is 1, 2 or 3, such that the cycloalkyl group is chosen from cyclopropyl, cyclobutyl and cyclopentyl, each optionally independently substituted by one to two $R_1$ or $R_2$;

ring A is:

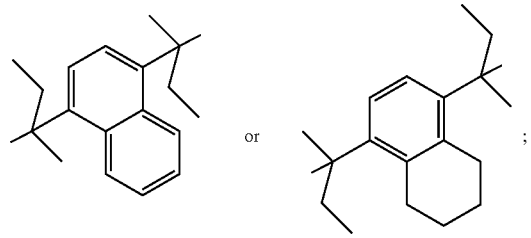

Q is
phenyl, pyridinyl, pyrimidinyl, pyridazinyl, imidazolyl, benzimidazolyl, thiazolyl, oxazolyl, naphthyridinyl, pyrazinyl, pyrazolyl, triazolyl, tetrazolyl, morpholinyl, thiomorpholinyl, thiomorpholinyl sulfoxide, thiomorpholinyl sulfone, piperazinyl, piperidinyl, piperidinonyl, dihydropyrimidonyl or tetrahydropyrimidonyl which are optionally substituted with one to three $C_{1-6}$ alkyl, phenyl, $C_{1-6}$ alkoxy or hydroxy;

$R_1$ is phenyl, morpholino, pyridinyl, pyrimidinyl, pyrazinyl, pyridazinyl, pyrrolyl, pyrrolidinyl, imidazolyl, pyrazolyl, thiazolyl, oxazoyl, [1,3,4]oxadiazol, triazolyl, tetrazolyl, isoxazolyl, isothiazolyl or indazolyl, each of the aforementioned is optionally substituted with one to three phenyl, naphthyl, heterocycle or heteroaryl as hereinabove described in this paragraph, $C_{1-6}$ branched or unbranched alkyl which is optionally partially or fully halogenated, $C_{3-7}$ cycloalkyl, bicyclopentanyl, bicyclohexanyl, bicycloheptanyl, phenyl $C_{1-5}$ alkyl, naphthyl $C_{1-5}$ alkyl, halogen, hydroxy, oxo, nitrile, $C_{1-3}$ alkoxy optionally partially or fully halogenated, phenyloxy, naphthyloxy, heteroaryloxy or heterocyclicoxy wherein the heterocyclic or heteroaryl moiety is as hereinabove described in this paragraph, nitro, amino, mono- or di-($C_{1-3}$alky)lamino, phenylamino, naphthylamino, heteroaryl or heterocyclic amino wherein the heteroaryl heterocyclic moiety is as hereinabove described in this paragraph, $NH_2C(O)$, a mono- or di-($C_{1-3}$alkyl) aminocarbonyl, $C_{1-5}$ alkyl-C(O)—$C_{1-4}$ alkyl, amino-$C_{1-5}$ alkyl, mono- or di-($C_{1-5}$alkyl)amino, mono- or di-($C_{1-3}$ alkyl)amino-$C_{1-5}$ alkyl, amino-$S(O)_2$ or di-($C_{1-3}$alkyl) amino-$S(O)_2$;

$C_{3-7}$ cycloalkyl, bicyclopentanyl, bicyclohexanyl or bicycloheptanyl, each being optionally be partially or fully halogenated and optionally substituted with one to three $C_{1-3}$ alkyl groups;

cyclopentenyl, cyclohexenyl, cycloheptenyl, cyclohexadienyl, cycloheptadienyl, bicyclohexenyl or bicycloheptenyl, each optionally substituted with one to three $C_{1-3}$ alkyl groups;

$C_{1-6}$ alkyl branched or unbranched and optionally partially or fully halogenated;

$R_2$, is a $C_{1-6}$ branched or unbranched alkyl optionally partially or fully halogenated, $C_{1-6}$acyl, aroyl, $C_{1-4}$ branched or unbranched alkoxy, each being optionally partially or fully halogenated, carboxy, nitrile, nitro, halogen.

In another embodiment of the invention there is provided compounds of the formula(I) as described immediately above, and wherein:

n is 1, such that the cycloalkyl group is cyclopropyl optionally independently substituted by one to two $R_1$ or $R_2$;

ring A is:

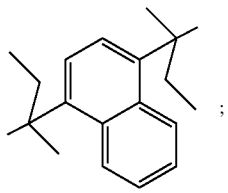

L is:
—O—, —S—, >C(O), >C(S), —OCH$_2$—, —CH$_2$—, —CH$_2$CH$_2$—, —CH$_2$CH$_2$CH$_2$—, —C(CH$_3$)$_2$—, —CH(OH)—, —CH$_2$CH(OH)—, —CH(OH)CH$_2$—, —OCH$_2$CH$_2$—, —OCH$_2$CH$_2$CH$_2$—, —OCH$_2$CH$_2$(CH$_3$)—, —OCH$_2$(CH$_3$)CH$_2$—, —OCH$_2$C(O)—, —CH=CH—CH$_2$—, —CH=CHCH$_2$CH$_2$, —NH—, —NHCH$_2$—, —NHCH$_2$CH$_2$—, —S(O)$_m$—, —S(O)$_m$CH$_2$—, —S(O)$_m$CH$_2$CH$_2$— and —S(O)$_m$CH$_2$CH$_2$CH$_2$—;

Q is phenyl, pyridinyl, pyrimidinyl, pyridazinyl, pyrazinyl, pyrazolyl, morpholinyl, thiomorpholinyl, thiomorpholinyl sulfoxide, thiomorpholinyl sulfone, piperazinyl, piperidinyl, piperidinonyl, dihydropyrimidonyl or tetrahydropyrimidonyl which are optionally substituted with one to three $C_{1-4}$ alkyl, phenyl, $C_{1-4}$ alkoxy or hydroxy;

$R_1$ is phenyl optionally substituted with one to three $C_{1-6}$ branched or unbranched alkyl which is optionally partially or fully halogenated, $C_{3-7}$ cycloalkyl, bicyclopentanyl, bicyclohexanyl, bicycloheptanyl, halogen, hydroxy, oxo, nitrile, $C_{1-3}$ alkoxy optionally partially or fully halogenated, nitro, amino or mono- or di-($C_{1-3}$alky)lamino;

$C_{3-7}$ cycloalkyl, bicyclopentanyl, bicyclohexanyl or bicycloheptanyl, each being optionally be partially or fully halogenated and optionally substituted with one to three $C_{1-3}$ alkyl groups;

cyclopentenyl, cyclohexenyl, cycloheptenyl, cyclohexadienyl, cycloheptadienyl, bicyclohexenyl or bicycloheptenyl, each optionally substituted with one to three $C_{1-3}$ alkyl groups;

$C_{1-6}$ alkyl branched or unbranched and optionally partially or fully halogenated; and $R_2$, is a $C_{1-6}$ branched or unbranched alkyl optionally partially or fully halogenated, $C_{1-4}$ branched or unbranched alkoxy, each being optionally partially or fully halogenated, carboxy, nitrile, nitro, halogen.

In yet another embodiment of the invention there is provided compounds of the formula(I) as described immediately above, and wherein:

L is:
—O—, —S—, >C(O), —OCH$_2$—, —CH$_2$—, —CH$_2$CH$_2$—, —CH$_2$CH$_2$CH$_2$—, —CH(OH)—, —CH$_2$CH(OH)—, —CH(OH)CH$_2$—, —OCH$_2$CH$_2$—, —OCH$_2$CH$_2$CH$_2$—, —OCH$_2$CH$_2$(CH$_3$)—, —OCH$_2$(CH$_3$)CH$_2$—, —S(O)$_m$—, —S(O)$_m$CH$_2$—, S(O)$_m$CH$_2$CH$_2$— and —S(O)$_m$CH$_2$CH$_2$CH$_2$—;

Q is pyridinyl, pyrimidinyl, dihydropyrimidonyl, morpholinyl, thiomorpholinyl, thiomorpholinyl sulfoxide or thiomorpholinyl sulfone which are optionally substituted with one to two $C_{1-4}$ alkoxy or $C_{1-4}$ alkyl;

$R_1$ is phenyl, $C_{3-7}$ cycloalkyl, bicyclopentanyl, bicyclohexanyl or bicycloheptanyl, each being optionally be partially or fully halogenated and optionally substituted with one to three $C_{1-3}$ alkyl groups;

$C_{1-6}$ alkyl branched or unbranched and optionally partially or fully halogenated; and $R_2$, is a $C_{1-6}$ branched or unbranched alkyl optionally partially or fully halogenated, $C_{1-4}$ branched or unbranched alkoxy, each being optionally partially or fully halogenated, carboxy, nitrile, nitro, halogen.

In still yet another embodiment of the invention there is provided compounds of the formula(I) as described immediately above, and wherein:

n is 1, such that the cycloalkyl group is cyclopropyl which is substituted by one $R_1$;

z is 0;

L is:
—O—, —S—, >C(O) and —OCH$_2$CH$_2$—;

Q is pyridinyl, pyrimidinyl, dihydropyrimidonyl or morpholinyl which are optionally substituted with one to two C$_{1-4}$ alkoxy or C$_{1-4}$ alkyl;

R$_1$ is phenyl, C$_{3-6}$ cycloalkyl or neopentyl each being optionally partially or fully halogenated.

In yet another embodiment of the invention there is provided compounds of the formula(I) as described immediately above, and wherein:

Q is pyridin-4-yl, pyrimidin-4-yl or morpholin-4-yl which are optionally substituted with one to two C$_{1-4}$ alkoxy or C$_{1-4}$ alkyl; and R$_1$ is phenyl, cyclohexyl or neopentyl each being optionally partially or fully halogenated.

In still yet another embodiment of the invention there is provided compounds of the formula(I) wherein:

n is 1, such that the cycloalkyl group is cyclopropyl which is substituted by one R$_1$;

z is 1;

Y is:
a bond, —O—, —S—, —CH$_2$—, >C(O), wherein each Y is further covalently attached to NR$_5$R$_6$, piperazinylC$_{0-2}$ alkyl, piperidinylC$_{0-2}$ alkyl, pyrrolidinylC$_{0-2}$ alkyl, each abovelisted heterocycle is optionally substituted by one to two acetyl, methyl, ethyl, halogen or hydroxy;

each R$_5$ and R$_6$ are independently hydrogen, C$_{3-5}$ cycloalkylC$_{1-2}$ alkyl, benzyl each optionally subtituted by chlorine, bromine, fluorine or C$_{1-2}$ alkyl, acetyl, benzoyl or C$_{1-4}$ branched or unbranched alkyl;

L is:
—O—, —S—, >C(O) and —OCH$_2$CH$_2$—;

Q is pyridinyl, triazinyl or pyrimidinyl which are optionally substituted with one to two C$_{1-4}$ alkoxy or C$_{1-4}$ alkyl;

R$_1$ is phenyl, C$_{3-6}$ cycloalkyl or neopentyl each being optionally partially or fully halogenated.

In yet another embodiment of the invention there is provided compounds of the formula(I) as described immediately above, and wherein:

L is —O—;

Q is pyridin-4-yl, pyrimidin-4-yl or triazin-2-yl which are optionally substituted with one to two C$_{1-4}$ alkoxy or C$_{1-4}$ alkyl; and R$_1$ is cyclohexyl and Y is:
a bond, —O—, —CH$_2$—, >C(O), wherein each Y is further covalently attached to NR$_5$R$_6$, piperazinyl, piperidinyl, pyrrolidinyl, each abovelisted heterocycle is optionally substituted by methyl, ethyl or hydroxy;

each R$_5$ and R$_6$ are independently hydrogen, cyclopropylmethyl, benzyl, benzoyl or C$_{1-3}$ alkyl.

Table I contains representative compounds of the invention wherein L is (i) which can be made by according to the general methods and examples in the sections below.

TABLE I

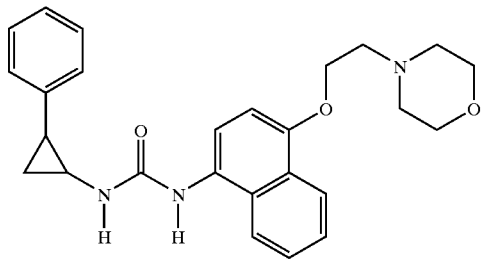

1-[4-(2-Morpholin-4-yl-ethoxy)-naphthalen-1-yl]-3-(2-phenyl-cyclopropyl)-urea;

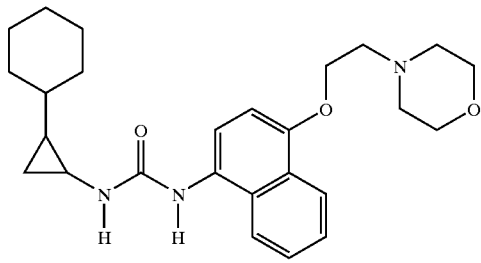

1-(2-Cyclohexyl-cyclopropyl)-3-[4-(2-morpholin-4-yl-ethoxy)-naphthalen-1-yl]-urea;

TABLE I-continued

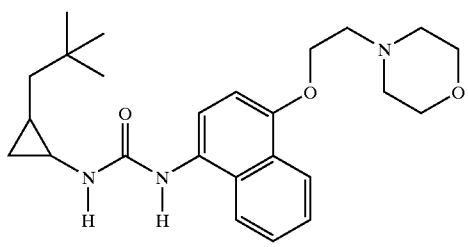
1-[2-(2,2-Dimethyl-propyl)-cyclopropyl]-3-[4-(2-morpholin-4-yl-ethoxy)-naphthalen-1-yl]-urea;

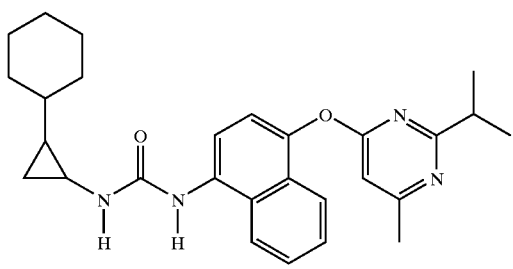
1-(2-Cyclohexyl-cyclopropyl)-3-[4-(2-isopropyl-6-methyl-pyrimidin-4-yloxy)-naphthalen-1-yl]-urea;

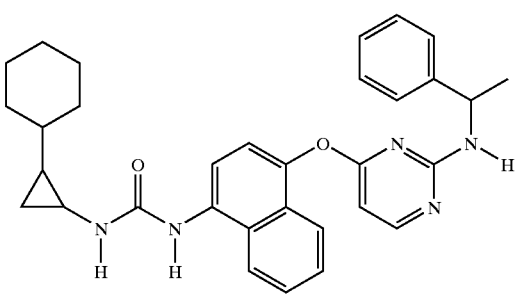
1-(2-Cyclohexyl-cyclopropyl)-3-{4-[2-(1-phenyl-ethylamino)-pyrimidin-4-yloxy]-naphthalen-1-yl}-urea;

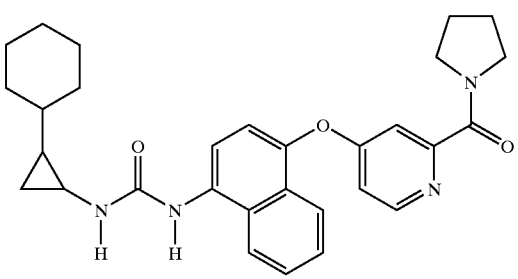
1-(2-Cyclohexyl-cyclopropyl)-3-{4-[2-(pyrrolidine-1-carbonyl)-pyridin-4-yloxy]-naphthalen-1-yl}-urea;

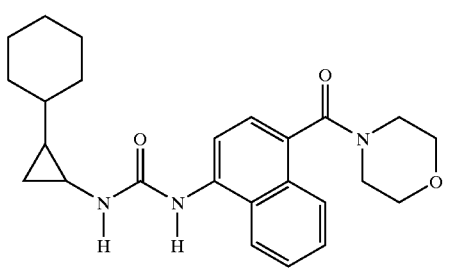
1-(2-Cyclohexyl-cyclopropyl)-3-[4-(morpholine-4-carbonyl)-naphthalen-1-yl]-urea;

TABLE I-continued

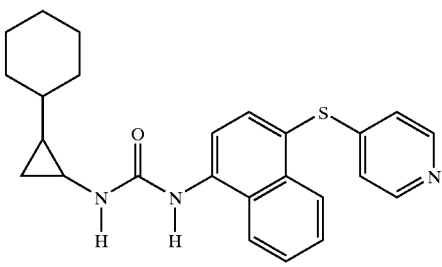
1-(2-Cyclohexyl-cyclopropyl)-3-[4-(pyridin-4-ylsulfanyl)-naphthalen-1-yl]-urea;

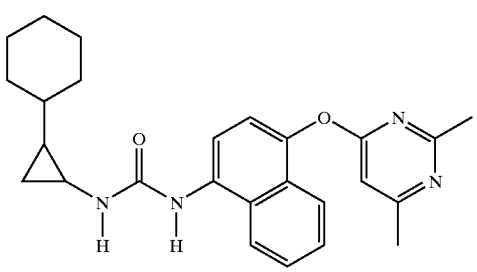
1-(2-Cyclohexyl-cyclopropyl)-3-[4-(2,6-dimethyl-pyrimidin-4-yloxy)-naphthalen-1-yl]-urea;

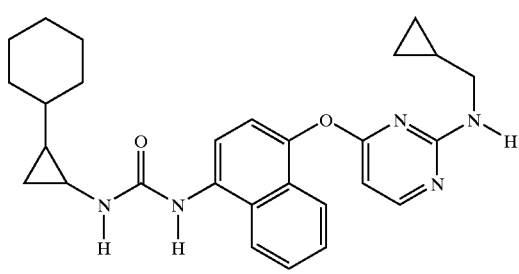
1-(2-Cyclohexyl-cyclopropyl)-3-{4-[2-(cyclopropylmethyl-amino)-pyrimidin-4-yloxy]-naphthalen-1-yl}-urea;

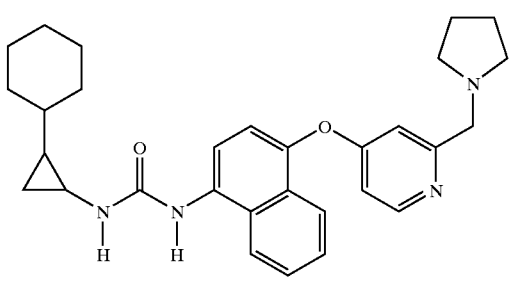
1-(2-Cyclohexyl-cyclopropyl)-3-[4-(2-pyrrolidin-1-ylmethyl-pyridin-4-yloxy)-naphthalen-1-yl]-urea;

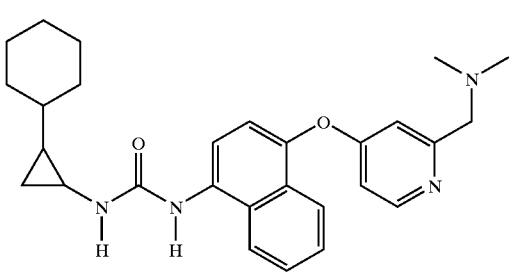
1-(2-Cyclohexyl-cyclopropyl)-3-[4-(2-dimethyl-aminomethyl-pyridin-4-yloxy)-naphthalen-1-yl]-urea;

TABLE I-continued

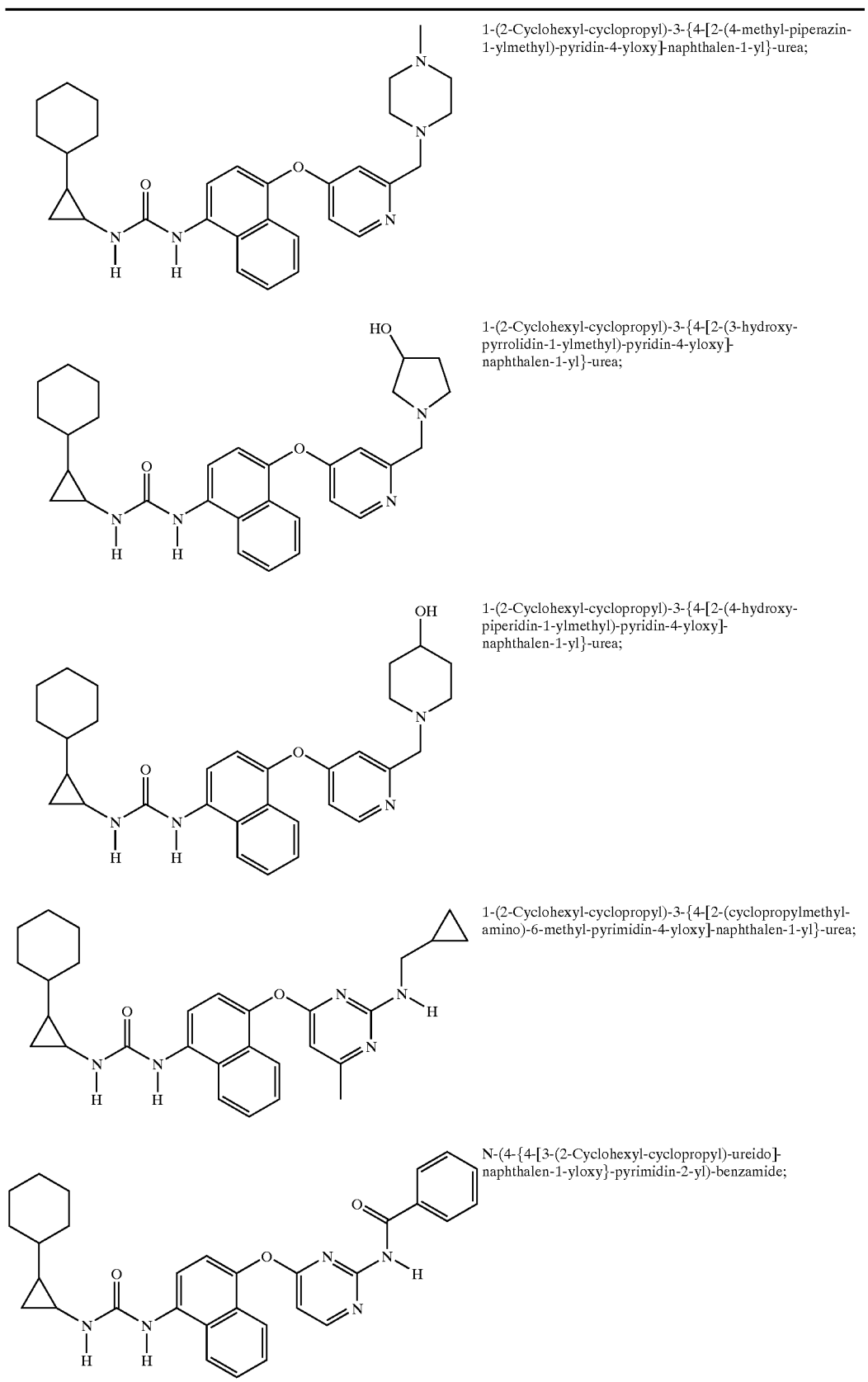

1-(2-Cyclohexyl-cyclopropyl)-3-{4-[2-(4-methyl-piperazin-1-ylmethyl)-pyridin-4-yloxy]-naphthalen-1-yl}-urea;

1-(2-Cyclohexyl-cyclopropyl)-3-{4-[2-(3-hydroxy-pyrrolidin-1-ylmethyl)-pyridin-4-yloxy]-naphthalen-1-yl}-urea;

1-(2-Cyclohexyl-cyclopropyl)-3-{4-[2-(4-hydroxy-piperidin-1-ylmethyl)-pyridin-4-yloxy]-naphthalen-1-yl}-urea;

1-(2-Cyclohexyl-cyclopropyl)-3-{4-[2-(cyclopropylmethyl-amino)-6-methyl-pyrimidin-4-yloxy]-naphthalen-1-yl}-urea;

N-(4-{4-[3-(2-Cyclohexyl-cyclopropyl)-ureido]-naphthalen-1-yloxy}-pyrimidin-2-yl)-benzamide;

TABLE I-continued

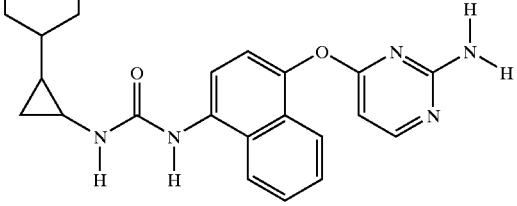

1-[4-(2-Amino-pyrimidin-4-yloxy)-naphthalen-1-yl]-3-(2-cyclohexyl-cyclopropyl)-urea;

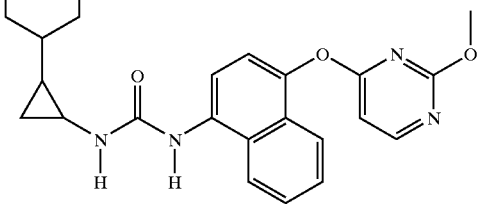

1-(2-Cyclohexyl-cyclopropyl)-3-[4-(2-methoxy-pyrimidin-4-yloxy)-naphthalen-1-yl]-urea;

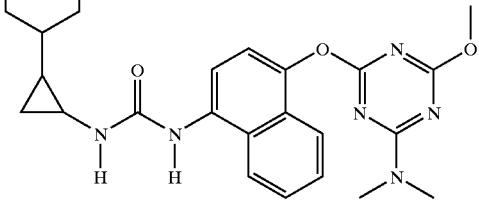

1-(2-Cyclohexyl-cyclopropyl)-3-[4-(4-dimethylamino-6-methoxy-[1,3,5]triazin-2-yloxy)-naphthalen-1-yl]-urea;

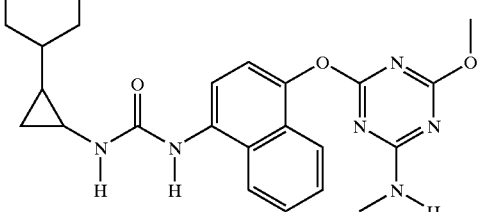

1-(2-Cyclohexyl-cyclopropyl)-3-[4-(4-methoxy-6-methylamino-[1,3,5]triazin-2-yloxy)-naphthalen-1-yl]-urea;

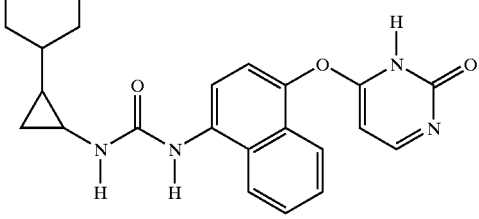

1-(2-Cyclohexyl-cyclopropyl)-3-[4-(2-oxo-2,3-dihydro-pyrimidin-4-yloxy)-naphthalen-1-yl]-urea;

TABLE I-continued

| Structure | Name |
|---|---|
| (structure) | 1-(2-Cyclohexyl-cyclopropyl)-3-{4-[2-(pyrrolidine-1-carbonyl)-pyridin-4-yloxy]-naphthalen-1-yl}-urea; |
| (structure) | 1-(2-Cyclohexyl-cyclopropyl)-3-[4-(2-oxo-2H-pyran-4-yloxy)-naphthalen-1-yl]-urea; |
| (structure) | 1-(2-Cyclohexyl-cyclopropyl)-3-[4-(1-methyl-2-oxo-1,2-dihydro-pyridin-4-yl)-naphthalen-1-yl]-urea | or the pharmaceutically acceptable derivatives thereof.

Table II contains further representative compounds of the invention wherein L is (i) which can be made by according to the general methods and examples in the sections below.

TABLE II

| Structure | Name |
|---|---|
| (structure) | 1-[4-(2-Amino-6-methyl-pyrimidin-4-yloxy)-naphthalen-1-yl]-3-(2-cyclohexyl-cyclopropyl)-urea |
| (structure) | 1-(2-Cyclohexyl-cyclopropyl)-3-{4-[2-(2-dimethylamino-ethylamino)-6-methyl-pyrimidin-4-yloxy]-naphthalen-1-yl}-urea |

TABLE II-continued

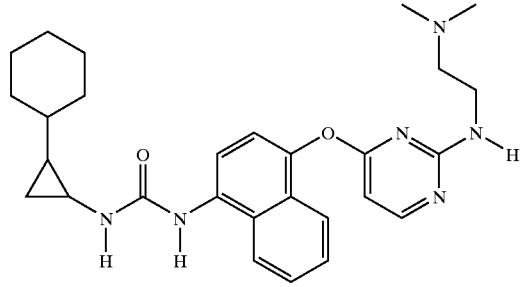

1-(2-Cyclohexyl-cyclopropyl)-3-{4-[2-(2-dimethylamino-ethylamino)-pyrimidin-4-yloxy]-naphthalen-1-yl}-urea

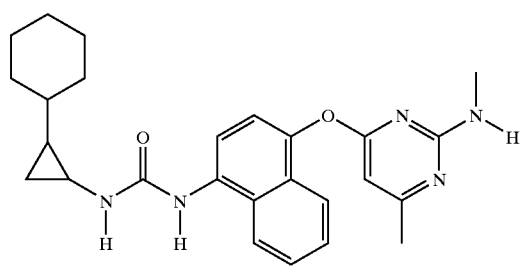

1-(2-Cyclohexyl-cyclopropyl)-3-[4-(6-methyl-2-methylamino-pyrimidin-4-yloxy)-naphthalen-1-yl]-urea

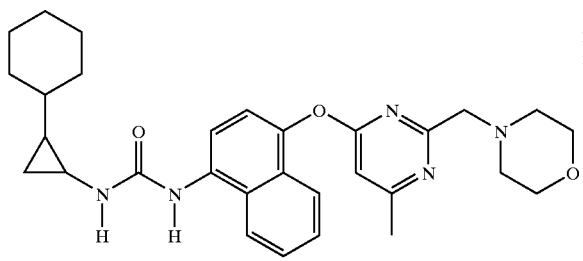

1-(2-Cyclohexyl-cyclopropyl)-3-[4-(6-methyl-2-morpholin-4-ylmethyl-pyrimidin-4-yloxy)-naphthalen-1-yl]-urea

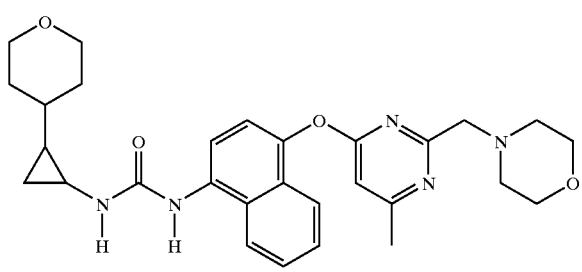

1-[4-(6-Methyl-2-morpholin-4-ylmethyl-pyrimidin-4-yloxy)-naphthalen-1-yl]-3-[2-(tetrahydro-pyran-4-yl)-cyclopropyl]-urea

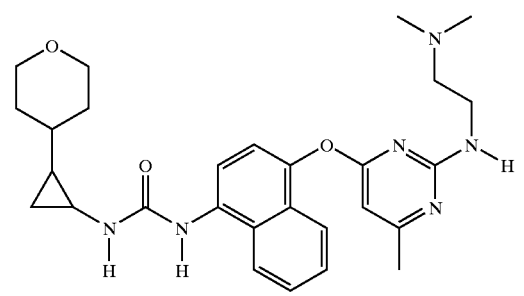

1-{4-[2-(2-Dimethylamino-ethylamino)-6-methyl-pyrimidin-4-yloxy]-naphthalen-1-yl}-3-[2-(tetrahydro-pyran-4-yl)-cyclopropyl]-urea or the pharmaceutically acceptable derivatives thereof.

In a second subgeneric aspect of the invention, there are provided compounds of the formula (I) as described in the broadest generic aspect and wherein:

L is (ii);
n is 1, 2, 3, such that the cycloalkyl group is chosen from cyclopropyl, cyclobutyl and cyclopentyl, each optionally independently substituted by one to two $R_1$ or $R_2$;
p is 0 or 1;
ring A is:

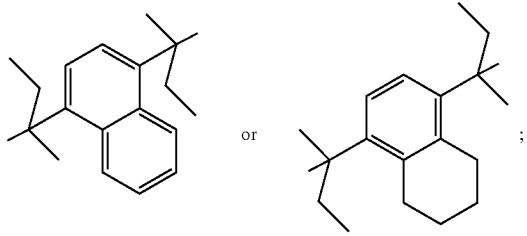

Q is
phenyl, pyridinyl, pyrimidinyl, pyridazinyl, imidazolyl, benzimidazolyl, thiazolyl, oxazolyl, naphthyridinyl, pyrazinyl, pyrazolyl, triazolyl, tetrazolyl, morpholinyl, thiomorpholinyl, thiomorpholinyl sulfoxide, thiomorpholinyl sulfone, piperazinyl, piperidinyl or tetrahydropyranyl which are optionally substituted with one to three $C_{1-6}$ alkyl, phenyl, $C_{1-6}$ alkoxy or hydroxy;
J is
—$CH_2$— or —$CH_2CH_2$—;
$R_1$ is
  phenyl, benzyl, tetrahydrofuranyl, tetrahydropyranyl, morpholino, pyridinyl, pyrimidinyl, piperidinyl, pyrazinyl, pyridazinyl, pyrrolyl, pyrrolidinyl, imidazolyl, pyrazolyl, thienyl, thiazolyl, oxazoyl, [1,3,4]oxadiazol, triazolyl, tetrazolyl, isoxazolyl, isothiazolyl or indazolyl, each of the aforementioned is optionally substituted with one to three phenyl, naphthyl, heterocycle or heteroaryl as hereinabove described in this paragraph, $C_{1-6}$ branched or unbranched alkyl which is optionally partially or fully halogenated, $C_{3-7}$ cycloalkyl$C_{0-2}$ alkyl, bicyclopentanyl, bicyclohexanyl, bicycloheptanyl, phenyl $C_{1-5}$ alkyl, $C_{1-5}$ acyl, $C_{1-5}$ alkoxycarbonyl, $C_{1-5}$ alkylS(O)$_m$—, naphthyl $C_{1-5}$ alkyl, halogen, hydroxy, oxo, nitrile, $C_{1-3}$ alkoxy optionally partially or fully halogenated, phenyloxy, naphthyloxy, heteroaryloxy or heterocyclicoxy wherein the heterocyclic or heteroaryl moiety is as hereinabove described in this paragraph, nitro, amino, mono- or di-($C_{1-3}$ alky)lamino, phenylamino, naphthylamino, heteroaryl or heterocyclic amino wherein the heteroaryl heterocyclic moiety is as hereinabove described in this paragraph, $NH_2C(O)$, a mono- or di-($C_{1-3}$alkyl) aminocarbonyl, $C_{1-5}$ alkyl-C(O)—$C_{1-4}$ alkyl, amino-$C_{1-5}$ alkyl, mono- or di-($C_{1-5}$alkyl)amino, mono- or di-($C_{1-3}$alkyl)amino-$C_{1-5}$ alkyl, amino-S(O)$_2$ or di-($C_{1-3}$alkyl)amino-S(O)$_2$;
$C_{3-7}$ cycloalkyl$C_{0-2}$ alkyl, bicyclopentanyl, bicyclohexanyl or bicycloheptanyl, each being optionally be partially or fully halogenated and optionally substituted with one to three $C_{1-3}$ alkyl groups;
  cyclopentenyl, cyclohexenyl, cycloheptenyl, cyclohexadienyl, cycloheptadienyl, bicyclohexenyl or bicycloheptenyl, each optionally substituted with one to three $C_{1-3}$ alkyl groups;
$C_{1-6}$ alkyl branched or unbranched and optionally partially or fully halogenated; and
$R_2$ is
a $C_{1-6}$ branched or unbranched alkyl optionally partially or fully halogenated, $C_{1-6}$acyl, aroyl, $C_{1-5}$ branched or unbranched alkoxy, each being optionally partially or fully halogenated, carboxy, nitrile, nitro, amino or halogen.

In another embodiment of the invention there is provided compounds of the formula(I) as described immediately above, and wherein:

n is 1, such that the cycloalkyl group is cyclopropyl optionally independently substituted by one to two $R_1$ or $R_2$;
ring A is:

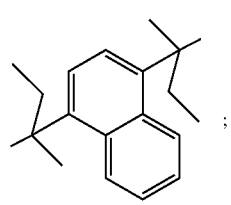

L is:
aryl, furanyl, thienyl, pyrrolyl, pyrazolyl, imidazolyl, pyridinyl, pyrimidinyl, pyridinonyl, dihydropyridinonyl, piperidinyl, benzimidazole, piperazinyl, pyridazinyl or pyrazinyl; each being optionally independently substituted with one to three $C_{1-4}$ alkyl, $C_{1-4}$alkoxy, oxo, hydroxy, nitrile, amino, mono- or di-($C_{1-3}$ alkyl)amino, mono- or di-($C_{1-3}$ alkylamino)carbonyl, $NH_2C(O)$, $C_{1-6}$ alkyl-S(O)$_m$ or halogen;
Q is
phenyl, pyridinyl, morpholinyl, thiomorpholinyl, thiomorpholinyl sulfoxide, thiomorpholinyl sulfone or tetrahydropyranyl each of which are optionally substituted with one to three $C_{1-4}$ alkyl, phenyl, $C_{1-4}$ alkoxy or hydroxy;
$R_1$ is
phenyl, benzyl, tetrahydrofuranyl, tetrahydropyranyl, morpholino, pyridinyl, piperidinyl, pyrrolidinyl or thienyl each of the aforementioned is optionally substituted with one to three phenyl, naphthyl, heterocycle or heteroaryl as hereinabove described in this paragraph, $C_{1-6}$ branched or unbranched alkyl which is optionally partially or fully halogenated, $C_{3-7}$ cycloalkyl$C_{0-2}$ alkyl, bicyclopentanyl, bicyclohexanyl, bicycloheptanyl, phenyl $C_{1-5}$ alkyl, $C_{1-5}$ acyl, $C_{1-5}$ alkoxycarbonyl, $C_{1-5}$ alkylS(O)$_m$—, naphthyl $C_{1-5}$ alkyl, halogen, hydroxy, oxo, nitrile, $C_{1-3}$ alkoxy optionally partially or fully halogenated, phenyloxy, naphthyloxy, heteroaryloxy or heterocyclicoxy wherein the heterocyclic or heteroaryl moiety is as hereinabove described in this paragraph, nitro, amino, mono- or di-($C_{1-3}$alky)lamino, phenylamino, naphthylamino, heteroaryl or heterocyclic amino wherein the heteroaryl heterocyclic moiety is as hereinabove described in this paragraph, $NH_2C(O)$, a mono- or di-($C_{1-3}$alkyl) aminocarbonyl, $C_{1-5}$ alkyl-C(O)—$C_{1-4}$ alkyl, amino-$C_{1-5}$ alkyl, mono- or di-($C_{1-5}$alkyl)amino, mono- or di-($C_{1-3}$alkyl)amino-$C_{1-5}$alkyl, amino-S(O)$_2$ or di-($C_{1-3}$alkyl) amino-S(O)$_2$;
$C_{3-7}$ cycloalkyl$C_{0-2}$ alkyl, bicyclopentanyl, bicyclohexanyl or bicycloheptanyl, each being optionally be partially or fully halogenated and optionally substituted with one to three $C_{1-3}$ alkyl groups;
$C_{1-6}$ alkyl branched or unbranched and optionally partially or fully halogenated; and R$_2$ is a C$_{1-6}$ branched or unbranched alkyl optionally partially or fully halogenated, C$_{1-5}$ branched or unbranched alkoxy, each being optionally partially or fully halogenated, carboxy, nitrile, nitro, halogen or amino.

In yet another embodiment of the invention there is provided compounds of the formula(I) as described immediately above, and wherein:

L is:

aryl, pyridinyl, pyrimidinyl or piperidinyl each being optionally independently substituted with one to three C$_{1-4}$ alkyl, C$_{1-4}$alkoxy, oxo, hydroxy, nitrile, amino, mono- or di-(C$_{1-3}$ alkyl)amino, mono- or di-(C$_{1-3}$ alkylamino) carbonyl, NH$_2$C(O), C$_{1-6}$ alkyl-S(O), or halogen;

Q is morpholinyl, thiomorpholinyl, thiomorpholinyl sulfoxide, thiomorpholinyl sulfone and tetrahydropyranyl each of which are optionally substituted with one to three C$_{1-4}$ alkyl;

R$_1$ is phenyl, benzyl, tetrahydrofuranyl, tetrahydropyranyl, pyrrolidinyl, piperidinyl or thienyl each of the aforementioned is optionally substituted with one to three C$_{1-6}$ branched or unbranched alkyl which is optionally partially or fully halogenated, C$_{3-7}$ cycloalkylC$_{0-2}$ alkyl, C$_{1-5}$ acyl, C$_{1-5}$ alkoxycarbonyl, C$_{1-5}$ alkylS(O)$_m$—, halogen, C$_{1-3}$ alkoxy, nitro, amino, mono- or di-(C$_{1-3}$alky)lamino, NH$_2$C(O) or a mono- or di-(C$_{1-3}$alkyl) aminocarbonyl;

C$_{3-7}$ cycloalkylC$_{0-2}$ alkyl optionally be partially or fully halogenated and optionally substituted with one to three C$_{1-3}$ alkyl groups;

C$_{1-6}$ alkyl branched or unbranched and optionally partially or fully halogenated; and R$_2$ is a C$_{1-6}$ branched or unbranched alkyl optionally partially or fully halogenated, C$_{1-5}$ branched or unbranched alkoxy, each being optionally partially or fully halogenated, halogen or amino.

In still yet another embodiment of the invention there is provided compounds of the formula(I) as described immediately above, and wherein:

n is 1, such that the cycloalkyl group is cyclopropyl which is substituted by one to two R$_1$ or R$_2$;

L is piperidinyl or 2-oxo-1,2-dihydropyridinyl;

Q is tetrahydropyranyl or morpholinyl which are optionally substituted with one to three C$_{1-4}$ alkyl;

R$_1$ is

C$_{1-5}$ alkyl, phenyl, benzyl, cyclohexylC$_{0-2}$ alkyl, cyclopentyl C$_{0-2}$ alkyl, tetrahydrofuranyl, thienyl, or R$_1$ is pyrrolidinyl or piperidinyl optionally substituted by C$_{1-4}$ acyl, C$_{1-5}$ alkoxycarbonyl or C$_{1-3}$ alkylsulfonyl; and R$_2$ is C$_{1-5}$ alkyl, C$_{1-5}$ alkoxy, halogen or amino.

In yet another embodiment of the invention there is provided compounds of the formula(I) as described immediately above, and wherein:

Q is tetrahydropyran-4-yl or morpholin-4-yl which are optionally substituted with one to three C$_{1-4}$ alkyl;

J is —CH$_2$—;

R$_1$ is neopentyl, tert-butyl, sec-butyl, 1,2-dimethylpropyl, isobutyl, phenyl, benzyl, cyclohexylC$_{0-1}$ alkyl, cyclopentyl C$_{0-1}$, alkyl, tetrahydrofuranyl, thienyl, or R$_1$ is pyrrolidinyl or piperidinyl optionally substituted by C$_{1-4}$ acyl, tert-butoxycarbonyl or C$_{1-2}$ alkylsulfonyl;

R$_2$ is methyl, methoxy, chlorine, bromine or amino; and

L is piperidin-3-yl or 2-oxo-1,2-dihydropyridin-4-yl.

Table III contains representative compounds of the invention wherein L is (ii) which can be made by according to the general methods and examples in the sections below.

TABLE III

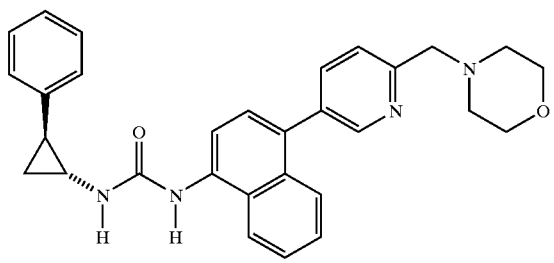

1-[4-(6-Morpholin-4-ylmethyl-pyridin-3-yl)-naphthalen-1-yl]-3-(2-phenyl-cyclopropyl)-urea;

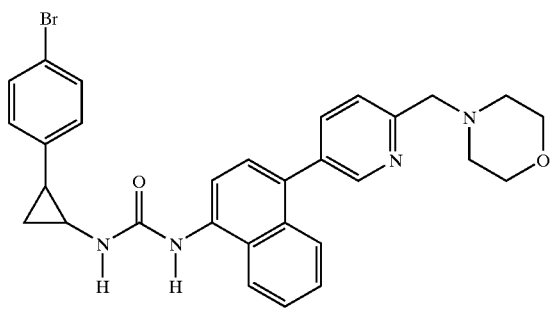

1-[2-(4-Bromo-phenyl)-cyclopropyl]-3-[4-(6-morpholin-4-ylmethyl-pyridin-3-yl)-naphthalen-1-yl]-urea;

TABLE III-continued

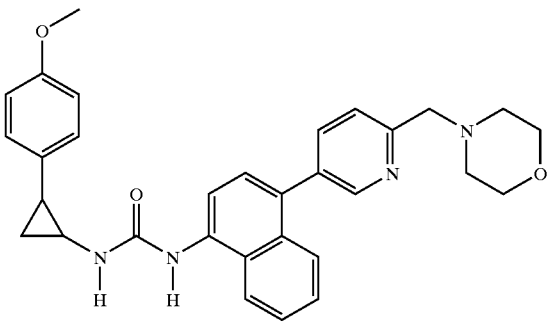

1-[2-(4-Methoxy-phenyl)-cyclopropyl]-3-[4-(6-morpholin-4-ylmethyl-pyridin-3-yl)-naphthalen-1-yl]-urea;

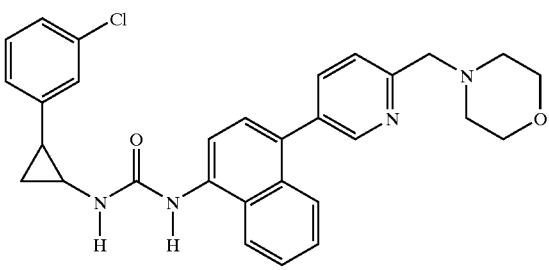

1-[2-(3-Chloro-phenyl)-cyclopropyl]-3-[4-(6-morpholin-4-ylmethyl-pyridin-3-yl)-naphthalen-1-yl]-urea;

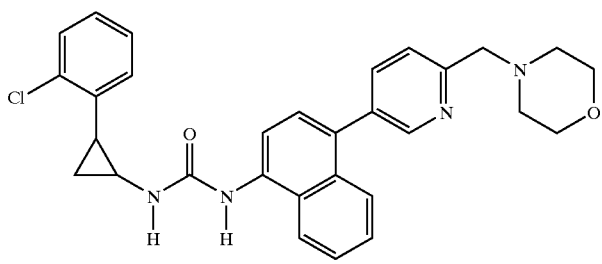

1-[2-(2-Chloro-phenyl)-cyclopropyl]-3-[4-(6-morpholin-4-ylmethyl-pyridin-3-yl)-naphthalen-1-yl]-urea;

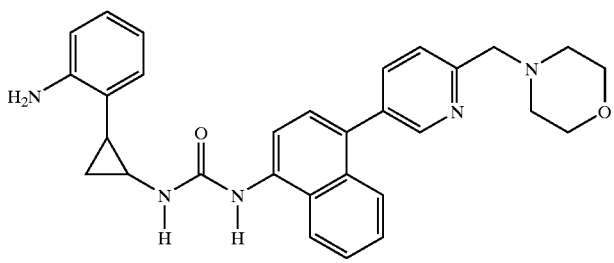

1-[2-(2-Amino-phenyl)-cyclopropyl]-3-[4-(6-morpholin-4-ylmethyl-pyridin-3-yl)-naphthalen-1-yl]-urea;

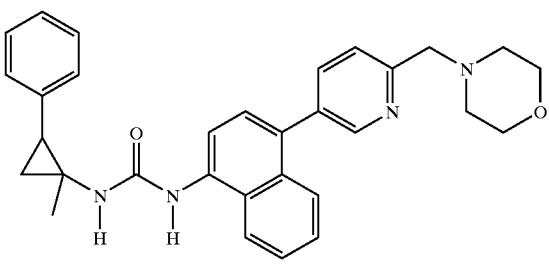

1-(1-Methyl-2-phenyl-cyclopropyl)-3-[4-(6-morpholin-4-ylmethyl-pyridin-3-yl)-naphthalen-1-yl]-urea;

TABLE III-continued

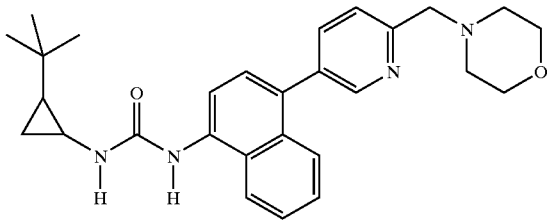
1-(2-tert-Butyl-cyclopropyl)-3-[4-(6-morpholin-4-ylmethyl-pyridin-3-yl)-naphthalen-1-yl]-urea;

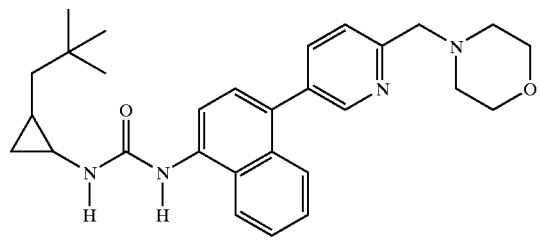
1-[2-(2,2-Dimethyl-propyl)-cyclopropyl]-3-[4-(6-morpholin-4-ylmethyl-pyridin-3-yl)-naphthalen-1-yl]-urea;

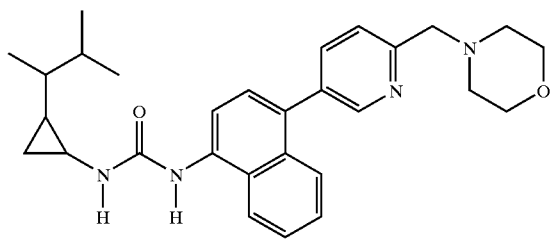
1-[2-(1,2-Dimethyl-propyl)-cyclopropyl]-3-[4-(6-morpholin-4-ylmethyl-pyridin-3-yl)-naphthalen-1-yl]-urea;

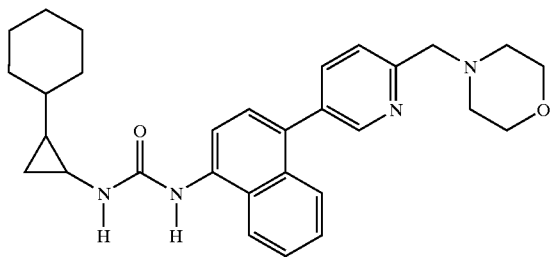
1-(2-Cyclohexyl-cyclopropyl)-3-[4-(6-morpholin-4-ylmethyl-pyridin-3-yl)-naphthalen-1-yl]-urea;

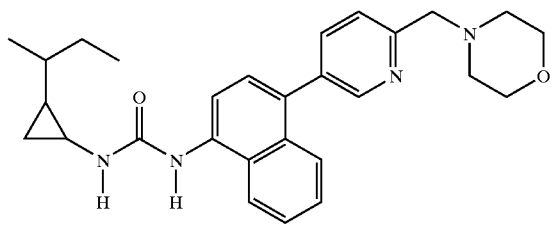
1-(2-sec-Butyl-cyclopropyl)-3-[4-(6-morpholin-4-ylmethyl-pyridin-3-yl)-naphthalen-1-yl]-urea;

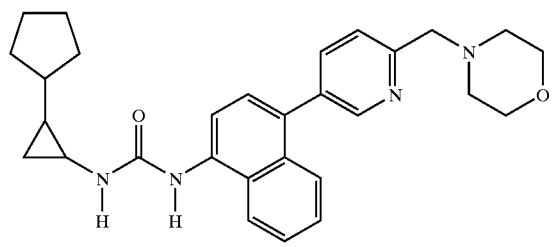
1-(2-Cyclopentyl-cyclopropyl)-3-[4-(6-morpholin-4-ylmethyl-pyridin-3-yl)-naphthalen-1-yl]-urea;

TABLE III-continued

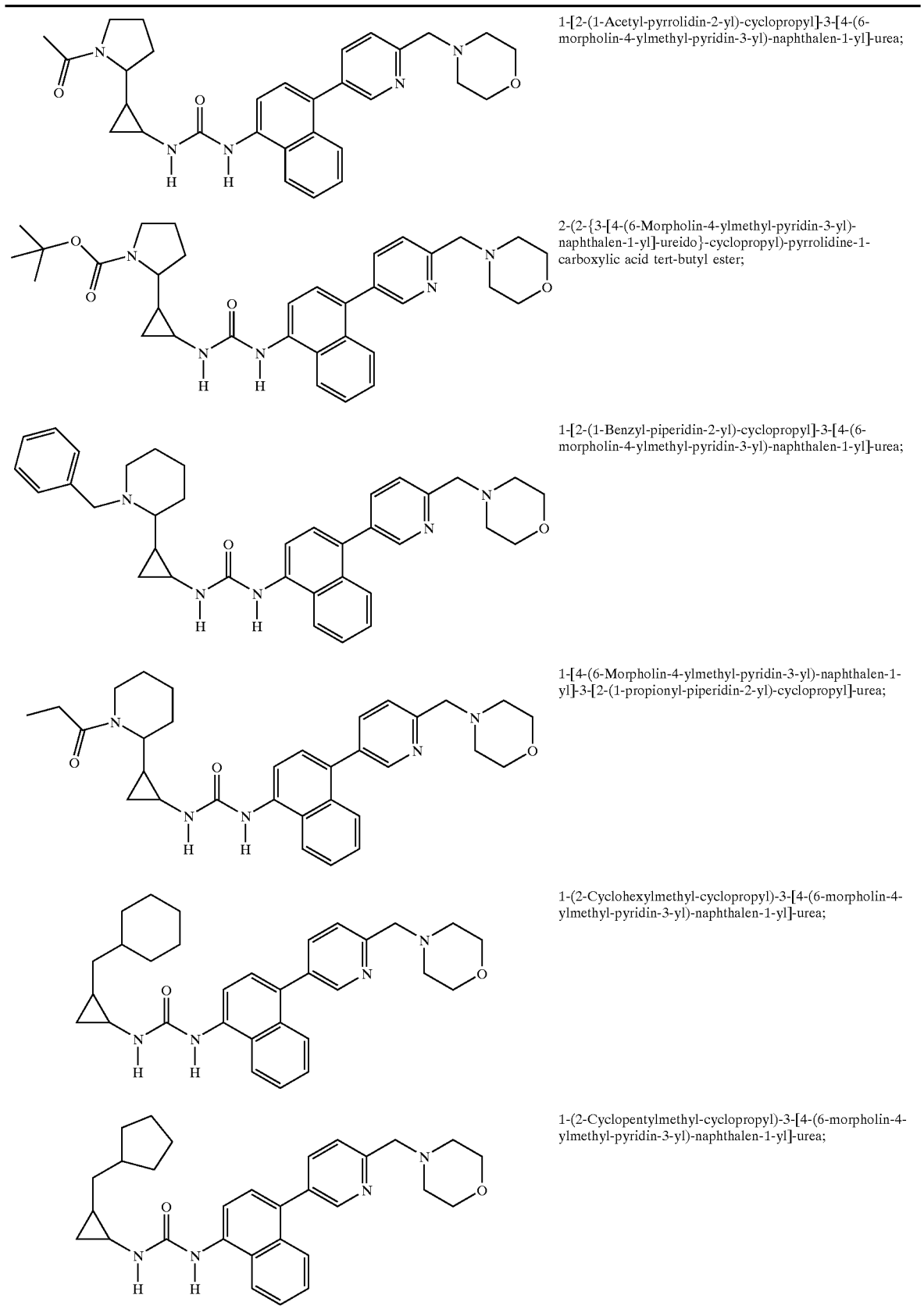

1-[2-(1-Acetyl-pyrrolidin-2-yl)-cyclopropyl]-3-[4-(6-morpholin-4-ylmethyl-pyridin-3-yl)-naphthalen-1-yl]-urea;

2-(2-{3-[4-(6-Morpholin-4-ylmethyl-pyridin-3-yl)-naphthalen-1-yl]-ureido}-cyclopropyl)-pyrrolidine-1-carboxylic acid tert-butyl ester;

1-[2-(1-Benzyl-piperidin-2-yl)-cyclopropyl]-3-[4-(6-morpholin-4-ylmethyl-pyridin-3-yl)-naphthalen-1-yl]-urea;

1-[4-(6-Morpholin-4-ylmethyl-pyridin-3-yl)-naphthalen-1-yl]-3-[2-(1-propionyl-piperidin-2-yl)-cyclopropyl]-urea;

1-(2-Cyclohexylmethyl-cyclopropyl)-3-[4-(6-morpholin-4-ylmethyl-pyridin-3-yl)-naphthalen-1-yl]-urea;

1-(2-Cyclopentylmethyl-cyclopropyl)-3-[4-(6-morpholin-4-ylmethyl-pyridin-3-yl)-naphthalen-1-yl]-urea;

TABLE III-continued

| | |
|---|---|
| 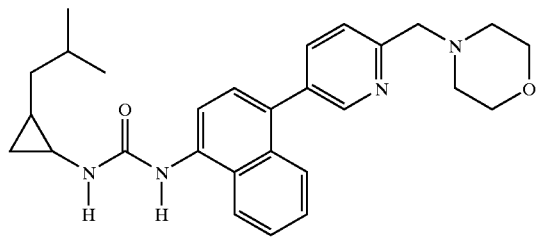 | 1-(2-Isobutyl-cyclopropyl)-3-[4-(6-morpholin-4-ylmethyl-pyridin-3-yl)-naphthalen-1-yl]-urea; |
| 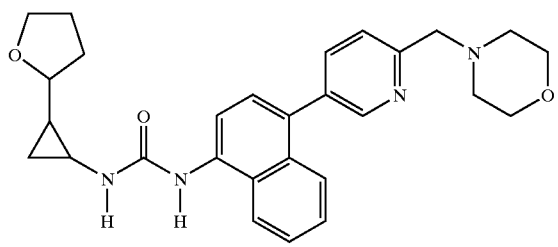 | 1-[4-(6-Morpholin-4-ylmethyl-pyridin-3-yl)-naphthalen-1-yl]-3-[2-(tetrahydro-furan-2-yl)-cyclopropyl]-urea; |
| 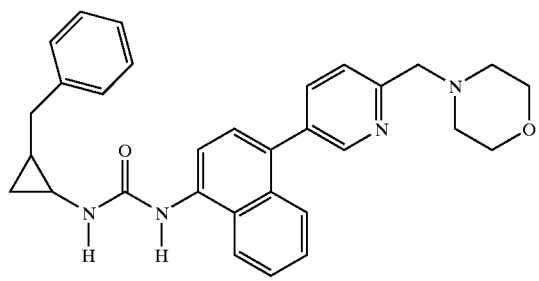 | 1-(2-Benzyl-cyclopropyl)-3-[4-(6-morpholin-4-ylmethyl-pyridin-3-yl)-naphthalen-1-yl]-urea; |
| 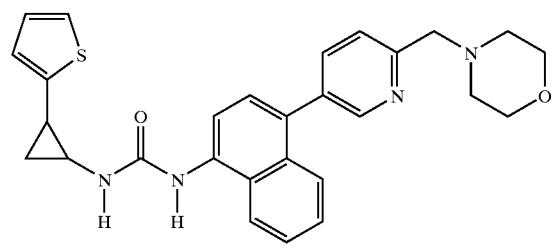 | 1-[4-(6-Morpholin-4-ylmethyl-pyridin-3-yl)-naphthalen-1-yl]-3-(2-thiophen-2-yl-cyclopropyl)-urea; |
| 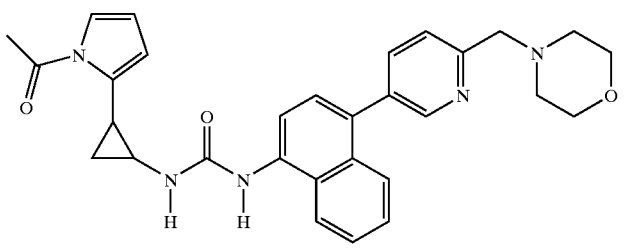 | 1-[2-(1-Acetyl-1H-pyrrol-2-yl)-cyclopropyl]-3-[4-(6-morpholin-4-ylmethyl-pyridin-3-yl)-naphthalen-1-yl]-urea; |
| 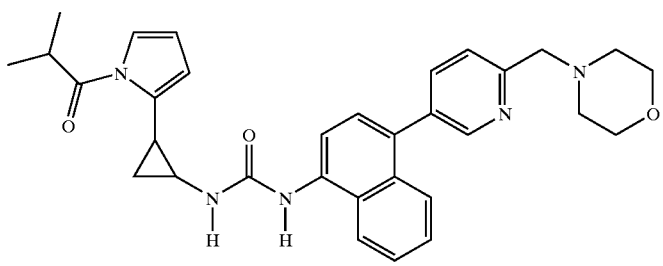 | 1-[2-(1-Isobutyryl-1H-pyrrol-2-yl)-cyclopropyl]-3-[4-(6-morpholin-4-ylmethyl-pyridin-3-yl)-naphthalen-1-yl]-urea; |

TABLE III-continued

| Structure | Name |
|---|---|
| 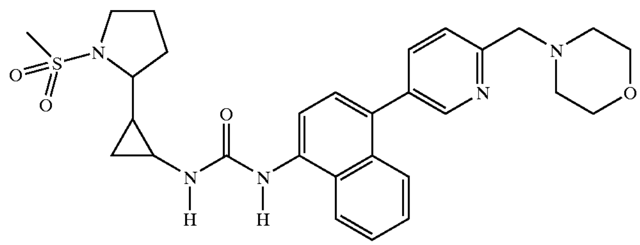 | 1-[2-(1-Methanesulfonyl-pyrrolidin-2-yl)-cyclopropyl]-3-[4-(6-morpholin-4-ylmethyl-pyridin-3-yl)-naphthalen-1-yl]-urea; |
| 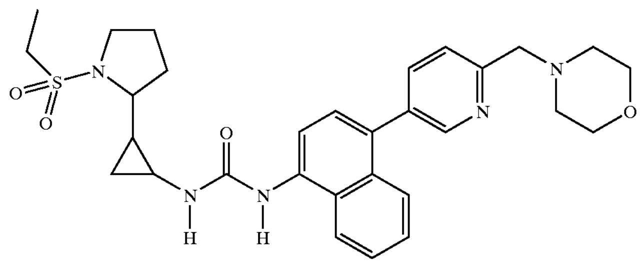 | 1-[2-(1-Ethanesulfonyl-pyrrolidin-2-yl)-cyclopropyl]-3-[4-(6-morpholin-4-ylmethyl-pyridin-3-yl)-naphthalen-1-yl]-urea; |
| 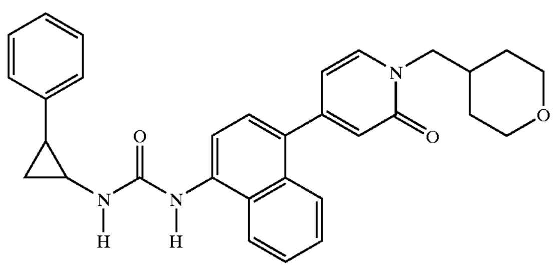 | 1-{4-[2-Oxo-1-(tetrahydro-pyran-4-ylmethyl)-1,2-dihydro-pyridin-4-yl]-naphthalen-1-yl}-3-(2-phenyl-cyclopropyl)-urea; |
| | 1-(2-Cyclohexyl-cyclopropyl)-3-{4-[2-oxo-1-(tetrahydro-pyran-4-ylmethyl)-1,2-dihydro-pyridin-4-yl]-naphthalen-1-yl}-urea | or the pharmaceuticaly acceptable derivatives thereof.

In all the compounds disclosed hereinabove in this application, in the event the nomenclature is in conflict with the structure, it shall be understood that the compound is defined by the structure.

Any compounds of this invention containing one or more asymmetric carbon atoms may occur as racemates and racemic mixtures, single enantiomers, diastereomeric mixtures and individual diastereomers. All such isomeric forms of these compounds are expressly included in the present invention. Each stereogenic carbon may be in the R or S configuration, or a combination of configurations.

Some of the compounds of formula (I) can exist in more than one tautomeric form. The invention includes all such tautomers.

All terms as used herein in this specification, unless otherwise stated, shall be understood in their ordinary meaning as known in the art. For example, "$C_{1-4}$alkoxy" is a $C_{1-4}$alkyl with a terminal oxygen, such as methoxy, ethoxy, propoxy, and butoxy. All alkyl, alkenyl and alkynyl groups shall be understood as being branched or unbranched where structurally possible and unless otherwise specified. Other more specific definitions are as follows:

The term "aroyl" as used in the present specification shall be understood to mean "benzoyl" or "naphthoyl".

The term "carbocycle" shall be understood to mean an aliphatic hydrocarbon radical containing from three to twelve carbon atoms. Carbocycles include hydrocarbon rings containing from three to ten carbon atoms. These carbocycles may be either aromatic or non-aromatic ring systems. The non-aromatic ring systems may be mono- or polyunsaturated. Preferred carbocycles unless otherwise specified include but are not limited to cyclopropyl, cyclobutyl, cyclopentyl, cyclopentenyl, cyclohexyl, cyclohexenyl, cycloheptanyl, cycloheptenyl, phenyl, indanyl, indenyl, benzocyclobutanyl, dihydronaphthyl, tetrahydronaphthyl, naphthyl, decahydronaphthyl, benzocycloheptanyl and benzocycloheptenyl.

The term "heterocycle" refers to a stable nonaromatic 4–8 membered (but preferably, 5 or 6 membered) monocyclic or nonaromatic 8–11 membered bicyclic heterocycle radical which may be either saturated or unsaturated. Each heterocycle consists of carbon atoms and one or more, preferably from 1 to 4 heteroatoms chosen from nitrogen, oxygen and sulfur. The heterocycle may be attached by any atom of the cycle, which results in the creation of a stable structure. Preferred heterocycles unless otherwise specified include but are not limited to, for example oxetanyl, pyrrolidinyl, tetrahydrofuranyl, tetrahydrothiophenyl, piperidinyl, piperazinyl, morpholinyl, tetrahydropyranyl, dioxanyl, tetramethylene sulfonyl, tetramethylene sulfoxidyl, oxazolinyl, thiazolinyl, imidazolinyl, tertrahydropyridinyl, homopiperidinyl, pyrrolinyl, tetrahydropyrimidinyl, decahydroquinolinyl, decahydroisoquinolinyl, thiomorpholinyl, thiazolidinyl, dihydrooxazinyl, dihydropyranyl, oxocanyl, heptacanyl, thioxanyl and dithianyl.

The term "heteroaryl" shall be understood to mean an aromatic 5–8 membered monocyclic or 8–11 membered bicyclic ring containing 1–4 heteroatoms chosen from N, O and S. Included are the partially or fully saturated derivates thereof. Such heteroaryls unless otherwise specified include: pyridinyl, pyridonyl, quinolinyl, dihydroquinolinyl, tetrahydroquinoyl, isoquinolinyl, tetrahydroisoquinoyl, pyridazinyl, pyrimidinyl, pyrazinyl, benzimidazolyl, benzothiazolyl, benzoxazolyl, benzofuranyl, benzothiophenyl, benzopyrazolyl, dihydrobenzofuranyl, dihydrobenzothiophenyl, benzooxazolonyl, benz[1,4]oxazin-3-onyl, benzodioxolyl, benz[1,3]dioxol-2-onyl, tetrahydrobenzopyranyl, indolyl, indolinyl, indolonyl, indolinonyl and phthalimidyl.

The term "heteroatom" as used herein shall be understood to mean atoms other than carbon such as O, N, S and P.

The term "aryl" as used herein unless otherwise specified shall be understood to mean aromatic carbocycle or heteroaryl as defined herein.

Terms which are analogs of the above cyclic moieties such as aryloxy, heterocyclyloxy or heteroaryl amine shall be understood to mean an aryl, heteroaryl, heterocycle as defined above attached to it's respective group.

As used herein, "nitrogen" and "sulfur" include any oxidized form of nitrogen and sulfur and the quaternized form of any basic nitrogen. For example, if Y is —S—$C_{1-6}$ alkyl, unless otherwise specified, this shall be understood to include —S(O)—$C_{1-6}$ alkyl and —S(O)$_2$—$C_{1-6}$ alkyl.

The term "halogen" as used in the present specification shall be understood to mean bromine, chlorine, fluorine or iodine. The definitions "partially or fully halogenated" "substituted by one or more halogen atoms" includes for example, mono, di or tri halo derivatives on one or more carbon atoms. For alkyl, a nonlimiting example would be —$CH_2CHF_2$, —$CF_3$ etc.

In all alkyl groups or carbon chains where one or more carbon atoms are optionally replaced by heteroatoms: O, S or N, it shall be understood that if N is not substituted then it is NH, it shall also be understood that the heteroatoms may replace either terminal carbon atoms or internal carbon atoms within a branched or unbranched carbon chain. Such groups can be substituted as herein above described by groups such as oxo to result in defintions such as but not limited to: alkoxycarbonyl, acyl, amido and thioxo.

The compounds of the invention are only those which are contemplated to be 'chemically stable' as will be appreciated by those skilled in the art. For example, a compound which would have a 'dangling valency', or a 'carbanion' are not compounds contemplated by the invention.

The invention includes pharmaceutically acceptable derivatives of compounds of formula (I). A "pharmaceutically acceptable derivative" refers to any pharmaceutically acceptable salt or ester of a compound of this invention, or any other compound which, upon administration to a patient, is capable of providing (directly or indirectly) a compound of this invention, a pharmacologically active metabolite or pharmacologically active residue thereof. A pharmacologically active metabolite shall be understood to mean any compound of the formula(I) capable of being metabolized enzymatically or chemically. This includes, for example, hydroxylated or oxidized derivative compounds of the formula(I).

Pharmaceutically acceptable salts of the compounds of this invention include those derived from pharmaceutically acceptable inorganic and organic acids and bases. Examples of suitable acids include hydrochloric, hydrobromic, sulfuric, nitric, perchloric, fumaric, maleic, phosphoric, glycolic, lactic, salicylic, succinic, toluene-p-sulfuric, tartaric, acetic, citric, methanesulfonic, formic, benzoic, malonic, naphthalene-2-sulfuric and benzenesulfonic acids. Other acids, such as oxalic acid, while not themselves pharmaceutically acceptable, may be employed in the preparation of salts useful as intermediates in obtaining the compounds of this invention and their pharmaceutically acceptable acid addition salts. Salts derived from appropriate bases include alkali metal (e.g., sodium), alkaline earth metal (e.g., magnesium), ammonium and N—($C_1$–$C_4$ alkyl)$_4^+$ salts.

In addition, the compounds of this invention include prodrugs of compounds of the formula (I). Prodrugs include those compounds that, upon simple chemical transformation, are modified to produce compounds of the invention. Simple chemical transformations include hydrolysis, oxidation and reduction. Specifically, when a prodrug of this invention is administered to a patient, the prodrug may be transformed into a compound of formula (I), thereby imparting the desired pharmacological effect.

METHODS OF USE

In accordance with the invention, there are provided methods of using the compounds of the formula (I). The compounds of the invention effectively block inflammatory cytokine production from cells. The inhibition of cytokine production is an attractive means for preventing and treating a variety of cytokine mediated diseases or conditions associated with excess cytokine production, e.g., diseases and pathological conditions involving inflammation. Thus, the compounds of the invention are useful for the treatment of such conditions. These encompass diseases including, but not limited to, rheumatoid arthritis, osteoarthritis, traumatic arthritis, multiple sclerosis, Guillain-Barre syndrome, Crohn's disease, ulcerative colitis, psoriasis, graft versus host disease, systemic lupus erythematosus, glomerulonephritis, reperfusion injury, sepsis, bone resorption diseases including osteoporosis, chronic obstructive pulmonary disease, congestive heart failure, Alzheimer's disease, atherosclerosis, toxic shock syndrome, asthma, contact dermatitis, percutaneous transluminal coronary angioplasty (PTCA) and insulin-dependent diabetes mellitus.

In addition, the compounds of the invention being inhibitors of cytokine production are expected to block inducible cyclooxygenase (COX-2) expression. COX-2 expression has been shown to be increased by cytokines and it is believed to be the isoform of cyclooxygenase responsible for inflammation (M. K. O'Banion et al., *Proc. Natl. Acad. Sci. U.S.A*, 1992, 89, 4888.) Accordingly, the present novel compounds would be expected to exhibit efficacy against those disorders currently treated with COX inhibitors such as the familiar NSAIDs. These disorders include acute and chronic pain as well as symptoms of inflammation and cardiovascular disease.

As discussed in the Background of the Invention, IL-8 plays a role in the influx of neutrophils into sites of inflammation or injury. Therefore, in a yet further aspect of the invention, the compounds of the invention may be useful in the treatment of diseases mediated predominantly by neutrophils such as stroke and myocardial infarction, alone or following thrombolytic therapy, thermal injury, adult respiratory distress syndrome (ARDS), multiple organ injury secondary to trauma, acute glomerulonephritis, dermatoses with acute inflammatory components, acute purulent meningitis or other central nervous system disorders, hemodialysis, leukopherisis, granulocyte transfusion associated syndromes, and necrotizing entrerocolitis.

For therapeutic use, the compounds of the invention may be administered in any conventional dosage form in any conventional manner. Routes of administration include, but are not limited to, intravenously, intramuscularly, subcutaneously, intrasynovially, by infusion, sublingually, transdermally, orally, topically or by inhalation. The preferred modes of administration are oral and intravenous.

The compounds of this invention may be administered alone or in combination with adjuvants that enhance stability of the inhibitors, facilitate administration of pharmaceutic compositions containing them in certain embodiments, provide increased dissolution or dispersion, increase inhibitory activity, provide adjunct therapy, and the like, including other active ingredients. Advantageously, such combination therapies utilize lower dosages of the conventional therapeutics, thus avoiding possible toxicity and adverse side effects incurred when those agents are used as monotherapies. Compounds of the invention may be physically combined with the conventional therapeutics or other adjuvants into a single pharmaceutical composition. Advantageously, the compounds may then be administered together in a single dosage form. In some embodiments, the pharmaceutical compositions comprising such combinations of compounds contain at least about 5%, but more preferably at least about 20%, of a compound of formula (I) (w/w) or a combination thereof. The optimum percentage (w/w) of a compound of the invention may vary and is within the purview of those skilled in the art. Alternatively, the compounds may be administered separately (either serially or in parallel). Separate dosing allows for greater flexibility in the dosing regime.

As mentioned above, dosage forms of the compounds of this invention include pharmaceutically acceptable carriers and adjuvants known to those of ordinary skill in the art. These carriers and adjuvants include, for example, ion exchangers, alumina, aluminum stearate, lecithin, serum proteins, buffer substances, water, salts or electrolytes and cellulose-based substances. Preferred dosage forms include, tablet, capsule, caplet, liquid, solution, suspension, emulsion, lozenges, syrup, reconstitutable powder, granule, suppository and transdermal patch. Methods for preparing such dosage forms are known (see, for example, H. C. Ansel and N. G. Popovish, *Pharmaceutical Dosage Forms and Drug Delivery Systems,* 5th ed., Lea and Febiger (1990)). Dosage levels and requirements are well-recognized in the art and may be selected by those of ordinary skill in the art from available methods and techniques suitable for a particular patient. In some embodiments, dosage levels range from about 1–1000 mg/dose for a 70 kg patient. Although one dose per day may be sufficient, up to 5 doses per day may be given. For oral doses, up to 2000 mg/day may be required. As the skilled artisan will appreciate, lower or higher doses may be required depending on particular factors. For instance, specific dosage and treatment regimens will depend on factors such as the patient's general health profile, the severity and course of the patient's disorder or disposition thereto, and the judgment of the treating physician.

In order that this invention be more fully understood, the following examples are set forth. These examples are for the purpose of illustrating preferred embodiments of this invention, and are not to be construed as limiting the scope of the invention in any way.

The examples which follow are illustrative and, as recognized by one skilled in the art, particular reagents or conditions could be modified as needed for individual compounds without undue experimentation. Starting materials used in the scheme below are either commercially available or easily prepared from commercially available materials by those skilled in the art.

General Synthetic Methods

The invention additionally provides for methods of making the compounds of the formula (I). The compounds of the invention may be prepared by the general methods and examples presented below, and methods known to those of ordinary skill in the art. Further reference in this regard may be made to U.S. Pat. Nos. 6,319,921 and 6,358,945, U.S. application Ser. Nos. 09/714,539, 09/611,109, 09/698,442, 09/834,797 and 09/902,085, and U.S. provisional application No. 60/283,642. Each of the aforementioned are incorporated herein by reference in their entirety. In all schemes, "G" in the formulas shown below shall have the meaning of the cycloalkyl group:

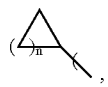

shown in the formula (I); and Ar in the definition of "G" in the formulas below shall have the meaning of the carbocyclic group:

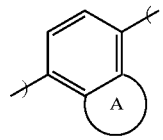

shown in the formula (I) of the invention described hereinabove.

The compounds of the invention may be prepared by Method A, B, C or D as illustrated in Scheme I.

Scheme I

Method A

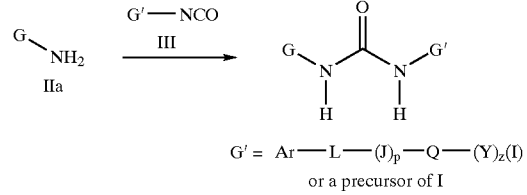

$G' = Ar-L-(J)_p-Q-(Y)_z(I)$
or a precursor of I

Method B

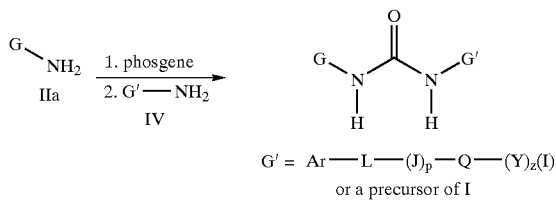

Method C

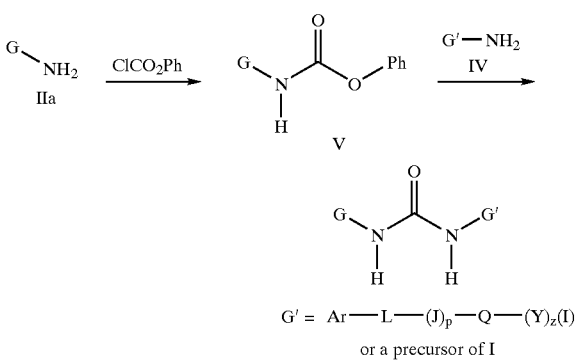

Method D

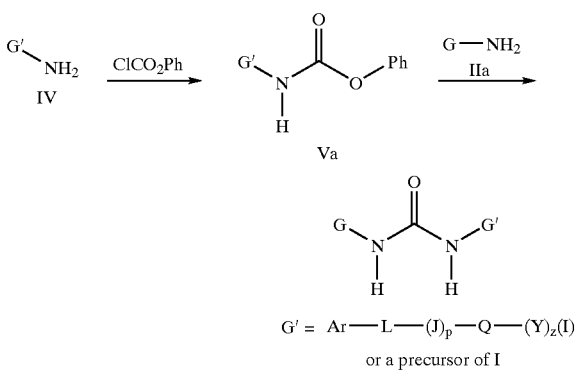

In Method A, a mixture of an amine of formula (Iia) and an arylisocyanate of formula (III) is dissolved in a non-protic, anhydrous solvent such as THF, ether, toluene, dioxane or ethyl acetate. The preferred solvent is THF. The mixture is stirred at between 0–45° C., preferably at 25° C., for 2–24 h, and the volatiles are removed. Purification of the residue by recrystallization from an appropriate solvent such as ethyl acetate/hexanes, ethyl acetate/MeOH, THF/petroleum ether, EtOH/water or by silica gel chromatography, using for example, hexanes and ethyl acetate as eluents, provides the product of formula (I) or precursors thereof.

In Method B, an amine of formula (IIa) is dissolved in a halogenated solvent, such as methylene chloride, chloroform or dichloroethane. The preferred solvent is methylene chloride. The mixture is diluted with aqueous alkali, such as sodium bicarbonate or potassium carbonate, cooled in an ice bath and phosgene is added. The mixture is vigorously stirred for 5–30 min, with 10 min being preferable. The organic layer is dried, with agents such as $MgSO_4$ or $Na_2SO_4$, and the volatiles removed to provide the corresponding isocyanate. The isocyanate and arylamine IV are mixed in a non-protic, anhydrous solvent such as THF, ether, toluene, dioxane, methylene chloride or ethyl acetate. The preferred solvent is THF. The mixture is stirred at between 0–45° C., preferably at 25° C., for 2–24 h, and the volatiles are removed. Purification of the residue by recrystallization or by silica gel chromatography, as above, provides the product of formula (I) or precursors thereof.

The required isocyanate may also be prepared from the carboxylic acid G—$CO_2$H by reaction with a chloroformate, such as ethyl chloroformate, in the presence of a suitable base, such as triethylamine, in a suitable solvent, such as THF at about 0° C. The resulting mixed anhydride is treated with an aqueous solution of sodium azide. Heating a solution of the resulting acyl azide in a suitable solvent, such as toluene, at about reflux, results in a Curtius rearrangement, providing the isocyanate G—N=C=O in situ. Preferably, the isocyanate may also be prepared by treatment of G—$CO_2$H with diphenyl phosphorazidate and a suitable base, such as triethylamine, in a suitable solvent, such as DME, to form the acyl azide, followed by heating to accomplish the Curtius rearrangement.

In Method C, an amine of formula (IIa) is dissolved in a suitable solvent such as a halogenated solvent which includes methylene chloride, chloroform or dichloroethane. The preferred solvent is methylene chloride. A suitable base such as triethylamine may be added, followed by an alkyl or aryl chloroformate, such as t-butyl chloroformate or phenyl chloroformate (shown). The mixture is stirred at between 0–85° C., preferably at reflux temperature, for 2–24 h, and the volatiles are removed providing carbamate (V). The carbamate and arylamine IV are mixed in a non-protic, anhydrous solvent such as THF, ether, toluene, dioxane, methylene chloride or ethyl acetate. The preferred solvent is THF. The mixture is stirred at between 0–110° C., preferably at reflux temperature, for 2–24 h, and the volatiles are removed. Purification of the residue as above provides the product of formula (I) or precursors thereof. This process can also be performed in the reverse sense as illustrated by Method D.

In Method D an arylamine of formula (IV) is dissolved in a suitable solvent such as a THF. A suitable alkyl or aryl chloroformate, such as t-butyl chloroformate or phenyl chloroformate (shown), is added. The mixture is stirred at between 0–85° C., preferably at 0° C., for 2–24 h, at which time the reaction is quenched with aqueous, saturated sodium bicarbonate. Extractions with a suitable solvent, such as ethyl acetate, provide carbamate Va upon concentration. The carbamate and amine IIa are mixed in a non-protic, anhydrous solvent such as THF, ether, toluene, dioxane, methylene chloride or ethyl acetate. The preferred solvent is THF. The mixture is stirred at between 0–110° C., preferably at 0° C., for 2–48 h, in a sealed tube. PS-trisamine and PS-isocynate resins are added, and the reaction mixture was shaken for 3 days. Filtration and concentration provides the product of formula (I) or precursors thereof.

Amine intermediates of formula (IIa) are either commercially available or can be made by methods known to those skilled in the art. Compounds of formula (I) with n=1 may be prepared by Method B, via the isocyanate as illustrated in Scheme II. An aldehyde bearing $R_1$ (or $R_2$) (VI) is treated with carbethoxymethylene triphenylphosphorane in a suitable solvent, such as THF, to provide the alpha, beta-unsaturated ester VII. Treatment with diazomethane in the presence of palladium (II) acetate in a suitable solvent, such as dichloromethane-ether, at about 0° C. to room temperature provides the cyclopropane carboxylic acid ester VIII. The ester is hydrolyzed to the corresponding carboxylic acid IX. Optionally the hydrolysis may be carried out prior to the cyclopropanation step. The carboxylic acid may then be converted to the isocyanate (X) via a Curtius rearrangement and reacted with the desired intermediate IV as described above for Method B.

Scheme II

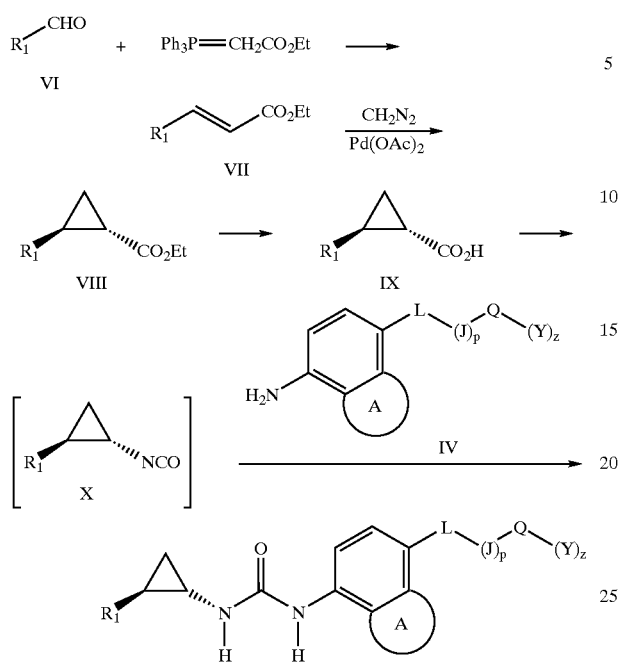

Methods by which intermediates III and IV, (Scheme I) may be prepared are known in the art. Several procedures are described and exemplified in the above-referenced patent applications.

SYNTHETIC EXAMPLES

Example 1

4-[5-(4-Aminonaphthyl)pyridin-2-ylmethyl]morpholine

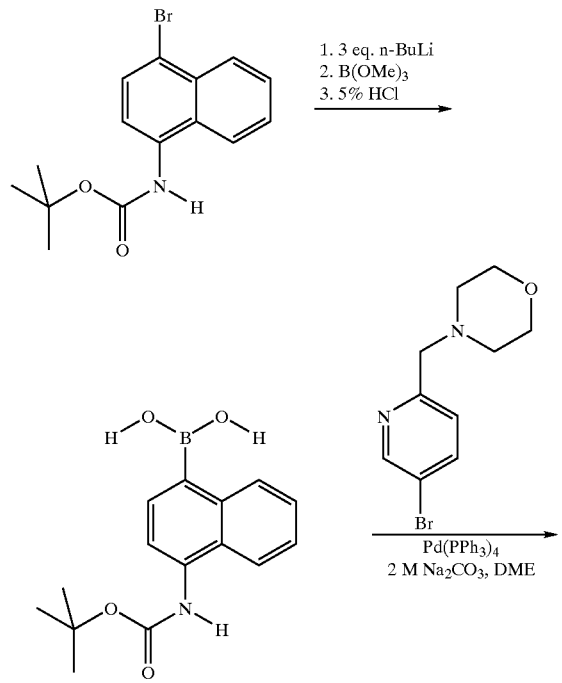

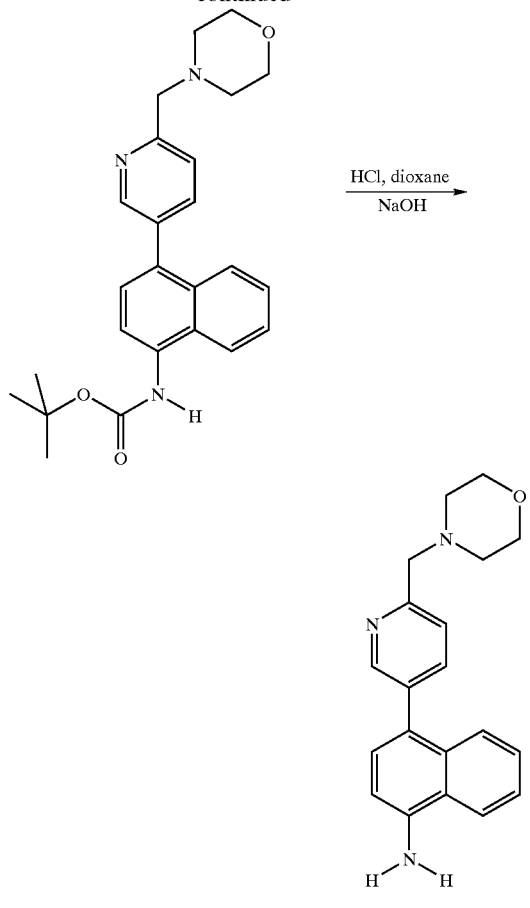

To a stirred solution of N-Boc-1-amino-4-bromo naphthalene (15.5 mmol) in anhydrous THF (40 mL) at −78° C. was added n-BuLi (47 mmol). The resultant yellow-green solution was stirred at −78° C. for two h then was transferred to a solution of trimethylborate (5.64 grams, 54.2 mmol) in anhydrous THF (25 mL) at −42° C. The reaction was allowed to warm to room temperature overnight as the bath warmed. After stirring for 16 h, 5% aqueous HCl was added (25 mL) and the mixture was stirred for 15 min. The aqueous layer was saturated with NaCl and the layers were separated. The aqueous portion was extracted with diethyl ether (3×60 mL) and the combined organics were extracted with 0.5 M NaOH (6×30 mL). The combined basic extracts were acidified to ~pH 2 with 3 M HCl (~30 mL) and the suspension was extracted with diethyl ether (3×100 mL). The combined ethereal extracts were dried (MgSO$_4$), filtered and the solvent was removed to afford the boronic acid as a beige solid (2.3 g) which was used without further purification.

This boronic acid (0.70 mmol) and 5-bromo-2-(morpholin-4-ylmethyl)pyridine (0.70 mmol) were dissolved in a biphasic mixture of dimethoxyethane (2 mL) and 2 M aq. Na$_2$CO$_3$ (1 mL). The reaction was purged with a stream of N$_2$ for 15 min, the Pd catalyst was added, and the mixture was heated at 85° C. for 16 h. The reaction was cooled to room temperature and was partitioned between water (10 mL) and EtOAc (75 mL). The layers were separated and the organic portion was washed with brine (20 mL), dried (MgSO$_4$), filtered and the solvent was removed to afford a brown solid. Column chromatography afforded the product as a beige solid.

This material (0.50 mmol) was dissolved in 2 mL anhydrous dioxane and HCl was added (2.5 mmol). The solution was stirred at room temperature for 16 h. To the resultant suspension was added diethyl ether (5 mL) and the mixture was chilled to 0° C. Neutralization with aq. NaOH and filtration afforded the title compound as a light brown solid (100 mg).

Example 2

1-[2-(3-Chloro-phenyl)-cyclopropyl]-3-[4-(6-morpholin-4-ylmethyl-pyridin-3-yl)-naphthalen-1-yl]-urea

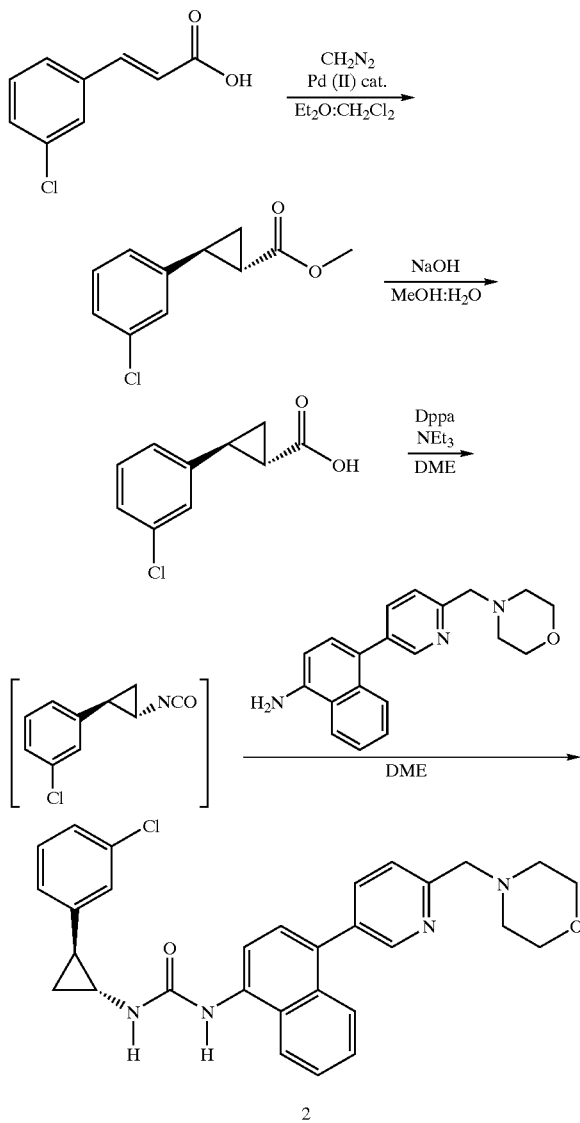

2

Diazomethane in ether was generated by adding portionwise N-nitroso-N-methyl urea to a biphasic mixture of ether (100 mL) and 2.5 M KOH in water (150 mL). The ether layer was transferred by pipette to a solution of 3-chlorocinnamic acid (1.00 g, 5.48 mmol, 1 equiv.) and palladium(II) acetate (6 mg, 0.028 mmol, 0.005 equiv.) in dichloromethane: ether (1:2, 150 mL) at 0° C. The addition was continued until a persistent yellow color remained in the solution. Stirring was continued for 2.5 h at 0° C., then approximately 3 mL acetic acid were added and the mixture was left standing at room temperature overnight. The resulting mixture was washed twice with saturated aqueous NaHCO$_3$ solution and once with brine. It was then dried (MgSO$_4$), filtered, and the solvent was removed in vacuo. The crude trans-2-(3-chlorophenyl)-cyclopropanecarboxylic acid methyl ester (1.09 g, 5.17 mmol, 94%) was obtained as a yellow oil.

The crude cyclopropanated ester from above (1.09 g, 5.17 mmol) was dissolved in 30 mL MeOH and treated with 15 mL of 2 M aqueous NaOH solution. The mixture was stirred at room temperature for 2 h. It was then placed on a rotary evaporator to remove the MeOH. The remaining solution was diluted with water (30 mL), washed with ether (15 mL), then acidified with 5 M aqueous HCl solution. The product was extracted with ether (3×40 mL) and the combined organics were washed with brine and dried (MgSO$_4$). After filtration, the solvents were removed in vacuo to afford 792 mg of 2-(3-chlorophenyl)-cyclopropanecarboxylic acid as a white solid (4.03 mmol, 78% yield).

Diphenyl phosphorazidate (0.21 mL, 0.98 mmol, 1.1 equiv.) and triethylamine (0.18 mL, 1.26 mmol, 1.4 equiv.) were added to a solution of cyclopropyl acid from above (176 mg, 0.90 mmol, 1 equiv.) in anhydrous DME (2.0 mL). The resulting mixture was stirred at 90° C. for 2.5 h. The resulting isocyanate solution was then cooled and treated with 4-(6-morpholin-4-ylmethyl-pyridin-3-yl)-naphthalen-1-ylamine (Example 1) in 1.5 mL anhydrous DME at room temperature. The mixture was left stirring overnight, then a few mL of MeOH were added and the solvents were removed in vacuo. The residue was purified by chromatography on SiO$_2$ column using 0–10% MeOH in dichloromethane as eluent. The material was isolated as a pale yellow foam (233 mg, 0.45 mmol, 68% yield) and was triturated in a hot acetonitrile/MeOH mixture to afford the title compound as a pale yellow powder in >98% purity by HPLC.

Example 3

1-(2-Cyclohexyl-cyclopropyl)-3-[4-(6-morpholin-4-ylmethyl-pyridin-3-yl)-naphthalen-1-yl]-urea

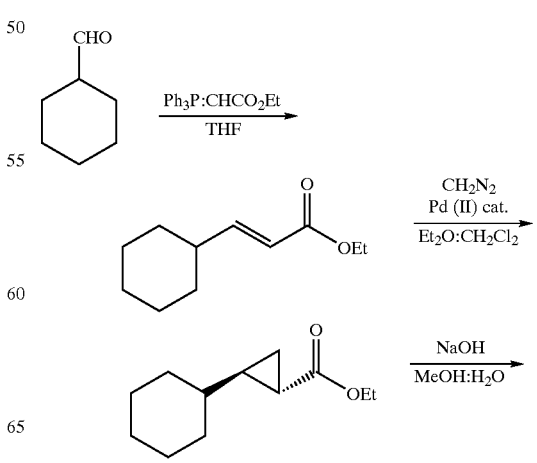

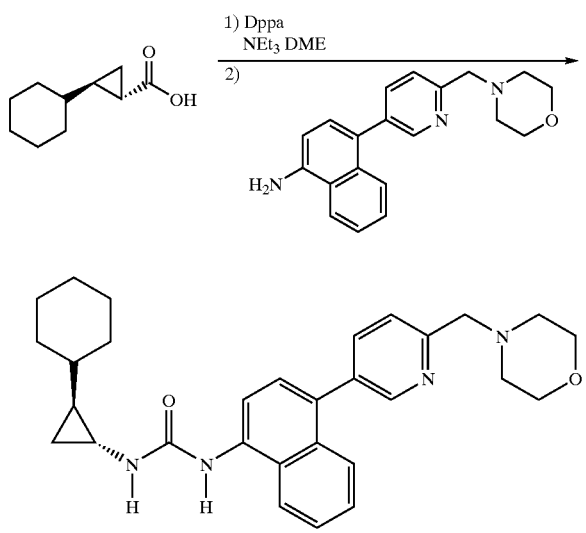

Cyclohexane carboxaldehyde (1.0 mL, 8.26 mmol, 1 equiv.) was dissolved in 30 mL anhydrous THF and treated with carbethoxy-methylene triphenylphosphorane (3.16 g, 9.08 mmol, 1.1 equiv.) at room temperature. The mixture was left stirring overnight, then quenched with saturated aqueous ammonium chloride, extracted 3 times with ether, and the combined organics were washed with brine. The solution was dried ($Na_2SO_4$), filtered and part of the solvents were removed in vacuo. Triphenylphosphine oxide crystallized out of the solution when left standing overnight. The residue was purified by column chromatography on $SiO_2$ to afford 1.51 g of α,β-unsaturated ester (quantitative yield).

Diazomethane in ether was generated by adding N-nitroso-N-methyl urea portionwise to a biphasic mixture of ether (100 mL) and 2.5 M KOH in water (150 mL). The yellow ether layer was transferred by pipette to a solution of the α,β-unsaturated ester from above (675 mg, 3.70 mmol, 1 equiv.) and palladium (II) acetate (4 mg, 0.019 mmol, 0.005 equiv.) in dichloromethane:ether (1:2, 100 mL) at 0° C. The addition was continued until a persistent yellow color remained in the solution. Stirring was continued for 2 h at 0° C., then approximately 1.5 mL acetic acid were added and the mixture was left to stand at room temperature overnight. The resulting mixture was washed twice with saturated aqueous $NaHCO_3$ solution and once with brine. It was then dried ($MgSO_4$), filtered, and the solvent was removed in vacuo. The crude trans-2-cyclohexyl-cyclopropanecarboxylic acid ethyl ester (726 mg, quantitative yield) was obtained as a yellow oil and used as is in the next step.

The crude ester (726 mg, 3.70 mmol, 1 equiv.) from above was dissolved in 20 mL MeOH and treated with 2.0 M aqueous NaOH solution (10 mL). The reaction mixture was stirred at room temperature for 3 h and then placed on a rotary evaporator to remove MeOH. Water was added and the mixture was washed once with ether. The aqueous layer was then acidified with 6 N HCl aqueous solution and the product was extracted with ether 3 times. The combined organics were washed once with brine, then dried ($MgSO_4$). The solution was filtered through a small plug of $SiO_2$ and the solvents removed in vacuo, providing 458 mg (2.72 mmol, 74%) of trans-2-cyclohexyl-cyclopropanecarboxylic acid.

Diphenylphosphoryl azide (0.18 mL, 0.83 mmol, 1.1 equiv.) and triethylamine (0.15 mL, 1.05 mmol, 1.4 equiv.) were added to a solution of the above acid (127 mg, 0.75 mmol, 1 equiv.) in anhydrous DME (2 mL). The solution was stirred at 90° C. for 2.5 h. The resulting yellow isocyanate solution was treated at room temperature with 4-(6-morpholin-4-ylmethyl-pyridin-3-yl)-naphthalen-1-ylamine (Example 1) in 1.5 mL anhydrous THF and left stirring for 18 h. MeOH was then added (2 mL) and the solvents were removed in vacuo. The crude product (a yellow oil) was purified by column chromatography on $SiO_2$ using 0–10% MeOH in dichloromethane as eluent. The title compound was obtained as a light yellow foam (75 mg, 0.15 mmol, 21%).

Example 4

1-[4-(2-Morpholin-4-yl-ethoxy)-naphthalen-1-yl]-3-(2-phenyl-cyclopropyl)-urea

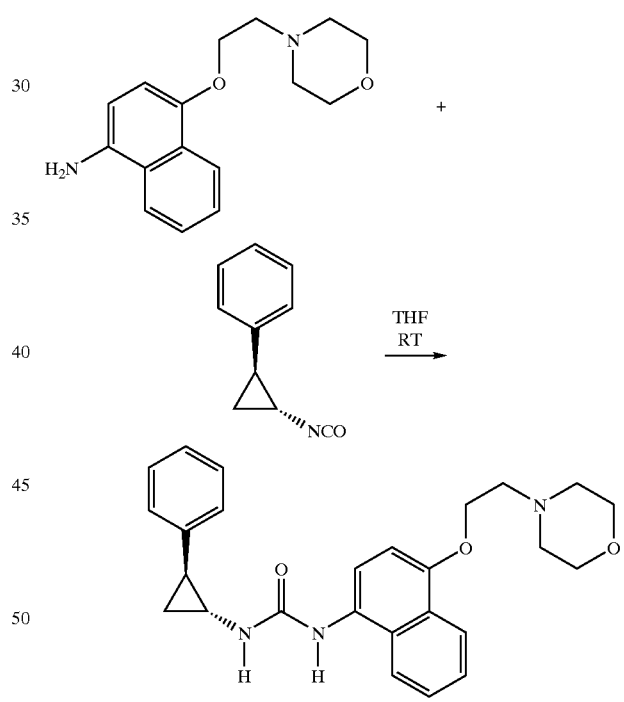

To 4-(2-morpholin-4-yl-ethoxy)-naphthalen-1-yl amine (165 mg, 0.61 mmol, 1 equiv.) dissolved in 2.5 mL anhydrous THF was added, via syringe, trans-2-phenyl-cyclopropyl-isocyanate (90 uL, 0.60 mmol, 1 equiv.). The mixture was left stirring at room temperature for 18 h under inert atmosphere, then the solvent was removed in vacuo. The product was purified by column chromatography on $SiO_2$, using 2–4% MeOH in EtOAc as eluent. A taupe foam was isolated, which recrystallized from hot acetonitrile to afford the title compound as a white solid (60 mg), mp 156–157° C.

What is claimed is:

1. A compound of the formula (I):

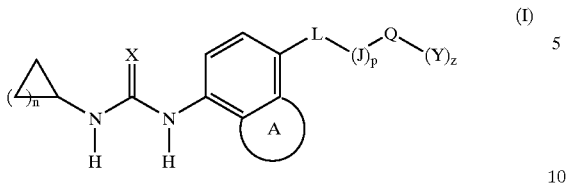

wherein:
n is 1, 2, 3, 4 or 5 such that the cycloalkyl group is chosen from cyclopropyl, cyclobutyl, cyclopentyl, cyclohexyl and cycloheptyl, each optionally independently substituted by one to two $R_1$ or $R_2$;

X is O;

p is 0;

z is 0;

m is 0, 1 or 2;

ring A is:
fused saturated or unsaturated ring containing 3–5 carbon atoms wherein ring A or the phenyl ring to which it is fused is optionally substituted by one or more $C_{1-6}$ branched or unbranched alkyl optionally partially or fully halogenated, acetyl, aroyl, $C_{1-6}$ branched or unbranched alkoxy optionally partially or fully halogenated, halogen, methoxycarbonyl, phenylsulfonyl, hydroxy, amino, mono- or di-($C_{1-4}$ alkyl)amino, mono- or di-($C_{1-4}$ alkyl)amino-S(O)$_2$, cyano, nitro or $H_2NSO_2$;

L is:
(i) an acyclic group chosen from —O—; —NH—; >C(O); >C(S);
$C_{1-10}$ saturated or unsaturated branched or unbranched carbon chain;
wherein one or more carbon atoms are optionally independently replaced by heteroatoms chosen from O, N and S(O)$_m$; and
wherein said acyclic group is optionally substituted with 0–2 oxo groups, one or more $C_{1-4}$ branched or unbranched alkyl optionally substituted by one or more halogen atoms, hydroxy, amino or imino;

Q is
pyrimidinyl optionally substituted with one to three oxo, $C_{1-6}$ alkyl, phenyl, $C_{1-6}$ alkoxy or hydroxyl;

$R_1$ is
phenyl, benzyl, naphthyl, pyrrolyl, pyrrolidinyl, imidazolyl, pyrazolyl, thiazolyl, oxazoyl, [1,3,4] oxadiazol, triazolyl, tetrazolyl, thienyl, furanyl, tetrahydrofuranyl, tetrahydropyranyl, isoxazolyl, isothiazolyl, benzimidazolyl, benzofuranyl, benzoxazolyl, benzisoxazolyl, benzpyrazolyl, benzothiofuranyl, each of the aforementioned is optionally substituted with one to three phenyl, naphthyl, heterocycle or heteroaryl as hereinabove described in this paragraph, $C_{1-6}$ branched or unbranched alkyl which is optionally partially or fully halogenated, $C_{3-7}$ cycloalkyl$C_{0-2}$ alkyl, bicyclopentanyl, bicyclohexanyl, bicycloheptanyl, phenyl $C_{1-5}$ alkyl, naphthyl $C_{1-5}$ alkyl, halogen, hydroxy, oxo, nitrile, $C_{1-3}$ alkoxy optionally partially or fully halogenated, phenyloxy, naphthyloxy, heteroaryloxy or heterocyclicoxy wherein the heterocyclic or heteroaryl moiety is as hereinabove described in this paragraph, nitro, amino, mono- or di-($C_{1-3}$alky)lamino, phenylamino, naphthylamino, heteroaryl or heterocyclic amino wherein the heteroaryl heterocyclic moiety is as hereinabove described in this paragraph, $NH_2C(O)$, a mono- or di-($C_{1-3}$alkyl) aminocarbonyl, $C_{1-5}$ alkyl-C(O)—$C_{1-4}$ alkyl, amino-$C_{1-5}$ alkyl, mono- or di-($C_{1-5}$alkyl)amino, mono- or di -($C_{1-3}$alkyl)amino-$C_{1-5}$ alkyl, $C_{1-5}$ alkyl-S(O)$_m$, amino-S(O)$_m$, di-($C_{1-3}$ alkyl)amino-S(O)$_m$, $R_3$—$C_{1-5}$ alkyl, $R_3$—$C_{1-5}$ alkoxy, $R_3$—C(O)—$C_{1-5}$ alkyl, $R_3$—$C_{1-5}$ alkyl($R_4$)N, $C_{1-6}$ acyl, $C_{1-6}$ alkoxy$C_{l-3}$ acyl, carboxy-mono- or di-($C_{1-5}$ alkyl)-amino;

$C_{3-7}$ cycloalkyl$C_{0-5}$ alkyl, bicyclopentanyl, bicyclohexanyl or bicycloheptanyl, each being optionally be partially or fully halogenated and optionally substituted with one to three $C_{1-3}$ alkyl groups;

cyclopentenyl, cyclohexenyl, cycloheptenyl, cyclohexadienyl, cycloheptadienyl, bicyclohexenyl or bicycloheptenyl, each optionally substituted with one to three $C_{1-3}$ alkyl groups;

$C_{1-4}$ alkyl-phenyl-C(O)—$C_{1-4}$ alkyl-, $C_{1-4}$ alkyl-C(O)—$C_{1-4}$ alkyl- or $C_{1-4}$ alkyl-phenyl-S(O)$_m$—$C_{1-4}$ alkyl-;

$C_{1-6}$ alkyl or $C_{1-6}$ alkoxy each of which is branched or unbranched and optionally partially or fully halogenated or optionally substituted with $R_3$;

$R_2$, is
a $C_{1-6}$ branched or unbranched alkyl optionally partially or fully halogenated, $C_{1-6}$acyl, aroyl, $C_{1-4}$ branched or unbranched alkoxy, each being optionally partially or fully halogenated, carboxy, nitrile, nitro, halogen, $C_{1-6}$ alkoxycarbonyl, $C_{1-6}$ alkyl-S(O)$_m$ optionally partially or fully halogenated, phenyl-S(O)$_m$, amino or aminocarbonyl wherein the N atom is optionally mono-or-disubstituted by $C_{1-6}$ branched or unbranched alkyl, $C_{1-6}$acyl, phenyl or benzyl;

each $R_3$ is independently:
nitrile, $C_{3-7}$ cycloalkyl, phenyl or $NR_5R_6$;

each $R_4$ is independently:
hydrogen or $C_{1-4}$ alkyl optionally partially or fully halogenated;

Y, is covalently attached to Q, and is
$C_{1-5}$ alkyl branched or unbranched, optionally substituted by one to three hydroxy, oxo, $C_{1-4}$ alkyl, $C_{1-3}$ alkoxy, $C_{1-4}$ acyl, $C_{1-5}$ alkoxycarbonyl, $NR_5R_6$ or $NR_5R_6$—C(O)—;

wherein Y is further covalently attached to morpholinyl optionally substituted by one to three hydroxy, oxo, $C_{1-3}$ alkyl, $C_{1-3}$ alkoxy, $C_{1-5}$ alkoxycarbonyl, $NR_5R_6$ or $NR_5R_6$—C(O)—;

each $R_5$ and $R_6$ are independently hydrogen, $C_{3-7}$ cycloalkyl$C_{0-4}$ alkyl, aryl$C_{0-3}$ alkyl optionally subtituted by halogen, $C_{1-3}$ alkyl or di$C_{1-5}$ alkyl amino, or $R_5$ and $R_6$ are $C_{1-3}$ acyl, aroyl or $C_{1-6}$ branched or unbranched alkyl optionally substituted by $C_{1-5}$ alkoxy, hydroxy, mono- or di-$C_{1-3}$alkylaminocarbonyl or mono or di$C_{1-3}$ alkyl amino wherein said $C_{1-6}$ alkyl optionally partially or fully halogenated;

and the pharmaceutically acceptable salts, tautomers or stereoisomers thereof.

2. The compound according to claim 1 wherein:

n is 1, 2 or 3, such that the cycloalkyl group is chosen from cyclopropyl, cyclobutyl and cyclopentyl, each optionally independently substituted by one to two $R_1$ or $R_2$;

ring A is:

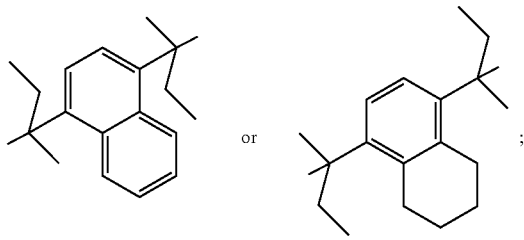

R$_1$ is
phenyl, pyrrolyl, pyrrolidinyl, imidazolyl, pyrazolyl, thiazolyl, oxazoyl, [1,3,4]oxadiazol, triazolyl, tetrazolyl, isoxazolyl or isothiazolyl each of the aforementioned is optionally substituted with one to three phenyl, naphthyl, heterocycle or heteroaryl as hereinabove described in this paragraph, C$_{1-6}$ branched or unbranched alkyl which is optionally partially or fully halogenated, C$_{3-7}$ cycloalkyl, bicyclopentanyl, bicyclohexanyl, bicycloheptanyl, phenyl C$_{1-5}$ alkyl, naphthyl C$_{1-5}$ alkyl, halogen, hydroxy, oxo, nitrile, C$_{1-3}$ alkoxy optionally partially or fully halogenated, phenyloxy, naphthyloxy, heteroaryloxy or heterocyclicoxy wherein the heterocyclic or heteroaryl moiety is as hereinabove described in this paragraph, nitro, amino, mono- or di-(C$_{1-3}$alky)lamino, phenylamino, naphthylamino, heteroaryl or heterocyclic amino wherein the heteroaryl heterocyclic moiety is as hereinabove described in this paragraph, NH$_2$C(O), a mono- or di-(C$_{1-3}$alkyl) aminocarbonyl, C$_{1-5}$ alkyl-C(O)—C$_{1-4}$ alkyl, amino-C$_{1-5}$ alkyl, mono- or di-(C$_{1-5}$ alkyl)amino, mono- or di-(C$_{1-3}$alkyl)amino-C$_{1-5}$ alkyl, amino-S(O)$_2$ or di-(C$_{1-3}$alkyl)amino-S(O)$_2$;

C$_{3-7}$ cycloalkyl, bicyclopentanyl, bicyclohexanyl or bicycloheptanyl, each being optionally be partially or fully halogenated and optionally substituted with one to three C$_{1-3}$ alkyl groups;

cyclopentenyl, cyclohexenyl, cycloheptenyl, cyclohexadienyl, cycloheptadienyl, bicyclohexenyl or bicycloheptenyl, each optionally substituted with one to three C$_{1-3}$ alkyl groups;

C$_{1-6}$ alkyl branched or unbranched and optionally partially or fully halogenated;

R$_2$, is
a C$_{1-6}$ branched or unbranched alkyl optionally partially or fully halogenated, C$_{1-6}$acyl, aroyl, C$_{1-4}$ branched or unbranched alkoxy, each being optionally partially or fully halogenated, carboxy, nitrile, nitro, halogen.

3. The compound according to claim 2 wherein:
n is 1, such that the cycloalkyl group is cyclopropyl optionally independently substituted by one to two R$_1$ or R$_2$;
ring A is:

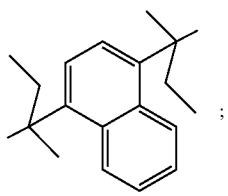

L is:
—O—, —S—, >C(O), >C(S), —OCH$_2$—, —CH$_2$—, —CH$_2$CH$_2$—, —CH$_2$CH$_2$CH$_2$—, —C(CH$_3$)$_2$—, —CH(OH)—, —CH$_2$CH(OH)—, —CH(OH)CH$_2$—, —OCH$_2$CH$_2$—, —OCH$_2$CH$_2$CH$_2$—, —OCH$_2$CH(CH$_3$)—, —OCH$_2$(CH$_3$)CH$_2$—, —OCH$_2$C(O)—, —CH═CH—CH$_2$—, —CH═CHCH$_2$CH$_2$, —NH—, —NHCH$_2$—, —NHCH$_2$CH$_2$—, —S(O)$_m$—, —S(O)$_m$CH$_2$—, —S(O)$_m$CH$_2$CH$_2$— and —S(O)$_m$CH$_2$CH$_2$CH$_2$—;

Q is
pyrimidinyl optionally substituted with one to three C$_{1-4}$ alkyl, phenyl, C$_{1-4}$ alkoxy or hydroxy;

R$_1$ is
phenyl optionally substituted with one to three C$_{1-6}$ branched or unbranched alkyl which is optionally partially or fully halogenated, C$_{3-7}$ cycloalkyl, bicyclopentanyl, bicyclohexanyl, bicycloheptanyl, halogen, hydroxy, oxo, nitrile, C$_{1-3}$ alkoxy optionally partially or fully halogenated, nitro, amino or mono- or di-(C$_{1-3}$alky)lamino;

C$_{3-7}$ cycloalkyl, bicyclopentanyl, bicyclohexanyl or bicycloheptanyl, each being optionally be partially or fully halogenated and optionally substituted with one to three C$_{1-3}$ alkyl groups;

cyclopentenyl, cyclohexenyl, cycloheptenyl, cyclohexadienyl, cycloheptadienyl, bicyclohexenyl or bicycloheptenyl, each optionally substituted with one to three C$_{1-3}$ alkyl groups;

C$_{1-6}$ alkyl branched or unbranched and optionally partially or fully halogenated; and R$_2$, is
a C$_{1-6}$ branched or unbranched alkyl optionally partially or fully halogenated, C$_{1-4}$ branched or unbranched alkoxy, each being optionally partially or fully halogenated, carboxy, nitrile, nitro, halogen.

4. The compound according to claim 3 wherein:
L is:
—O—, —S—, >C(O), —OCH$_2$—, —CH$_2$—, —CH$_2$CH$_2$—, —CH$_2$CH$_2$CH$_2$—, —CH(OH)—, —CH$_2$CH(OH)—, —CH(OH)CH$_2$—, —OCH$_2$CH$_2$—, —OCH$_2$CH$_2$CH$_2$—, —OCH$_2$CH$_2$(CH$_3$)—, —OCH$_2$(CH$_3$)CH$_2$—, —S(O)$_m$—, —S(O)$_m$ CH$_2$—, —S(O)$_m$CH$_2$CH$_2$— and —S(O)$_m$CH$_2$CH$_2$CH$_2$—;

Q is
pyrimidinyl, optionally substituted with one to two C$_{1-4}$ alkoxy or C$_{1-4}$ alkyl;

R$_1$ is
phenyl, C$_{3-7}$ cycloalkyl, bicyclopentanyl, bicyclohexanyl or bicycloheptanyl, each being optionally be partially or fully halogenated and optionally substituted with one to three C$_{1-3}$ alkyl groups;

C$_{1-6}$ alkyl branched or unbranched and optionally partially or fully halogenated; and R$_2$, is
a C$_{1-6}$ branched or unbranched alkyl optionally partially or fully halogenated, C$_{1-4}$ branched or unbranched alkoxy, each being optionally partially or fully halogenated, carboxy, nitrile, nitro, halogen.

5. The compound according to claim 4 wherein:
n is 1, such that the cycloalkyl group is cyclopropyl which is substituted by one R$_1$;
L is:
—O—, —S—, >C(O) and —OCH$_2$CH$_2$—;
R$_1$ is phenyl, $C_{3-6}$ cycloalkyl or neopentyl each being optionally partially or fully halogenated.

6. The compound according to claim 5 wherein:

Q is
   pyrimidin-4-yl optionally substituted with one to two $C_{1-4}$ alkoxy or $C_{1-4}$ alkyl; and $R_1$ is
   phenyl, cyclohexyl or neopentyl each being optionally partially or fully halogenated.

7. The compound according to claim 6 wherein:

Y is:
   optionally substituted by one to two acetyl, methyl, ethyl, halogen or hydroxy;
   each $R_5$ and $R_6$ are independently hydrogen, $C_{3-5}$ cycloalkyl$C_{1-2}$ alkyl, benzyl each optionally subtituted by chlorine, bromine, fluorine or $C_{1-2}$ alkyl, acetyl, benzoyl or $C_{1-4}$ branched or unbranched alkyl;

L is:
   —O—, —S—, >C(O) and —OCH$_2$CH$_2$—;

$R_1$ is
   phenyl, $C_{3-6}$ cycloalkyl or neopentyl each being optionally partially or fully halogenated.

8. The compound according to claim 7 wherein:

L is —O—;

$R_1$ is cyclohexyl and
   each $R_5$ and $R_6$ are independently hydrogen, cyclopropylmethyl, benzyl, benzoyl or $C_{1-3}$ alkyl.

9. A compound selected from:
1-[4(2-Morpholin-4-yl-ethoxy)-naphthalen-1-yl]-3-(2-phenyl-cyclopropyl)-urea;
1-(2-Cyclohexyl-cyclopropyl)-3-[4-(2-morpholin-4-yl-ethoxy)-naphthalen-1-yl]-urea and
1-[2-(2,2-Dimethyl-propyl)-cyclopropyl]-3-[4-(2-morpholin-4-yl-ethoxy)-naphthalen-1-yl]-urea;
or the pharmaceutically acceptable salts, tautomers or stereoisomers thereof.

10. A compound selected from:
1-(2-Cyclohexyl cyclopropyl)-3-[4(6methyl-2-morpholin-4-ylmethyl-pyrimidin-4-yloxy) -naphthalen-1-yl]urea;
or the pharmaceutically acceptable derivatives thereof.

11. A pharmaceutical composition comprising a pharmaceutically effective amount of a compound according to claim 1.

12. A method of treating a cytokine mediated disease or condition which comprises administering to a patient in need of such treatment a therapeutically effective amount of a compound according to claim 1.

13. The method according to claim 12 wherein cytokine mediated disease or condition is selected from rheumatoid arthritis, inflammatory bowel disease, septic shock, osteoarthritis, Crohn's disease, ulcerative colitis, multiple sclerosis, Guillain-Barre syndrome, psoriasis, graft versus host disease, systemic lupus erythematosus, percutaneous transluminal coronary angioplasty, diabetes, toxic shock syndrome, Alzheimer's disease, acute and chronic pain, contact dermatitis, atherosclerosis, traumatic arthritis, glomerulonephritis, reperfusion injury, sepsis, bone resorption diseases, chronic obstructive pulmonary disease, congestive heart failure, asthma, stroke, myocardial infarction, thermal injury, adult respiratory distress syndrome (ARDS), multiple organ injury secondary to trauma, dermatoses with acute inflammatory components, acute purulent meningitis, necrotizing entrerocolitis, syndromes associated with hemodialysis, leukopherisis and granulocyte transfusion.

14. The method according to claim 13 wherein the disease is selected from rheumatoid arthritis, osteoarthritis, Crohn's disease, psoriasis, ulcerative colitis, osteoporosis, chronic obstructive pulmonary disease, percutaneous transluminal coronary angioplasty and congestive heart failure.

15. The method according to claim 14 wherein the disease is selected from rheumatoid arthritis, Crohn's disease, psoriasis, chronic obstructive pulmonary disease, percutaneous transluminal coronary angioplasty and congestive heart failure.

16. A process of making a compound of the formula (I) according to claim 1,

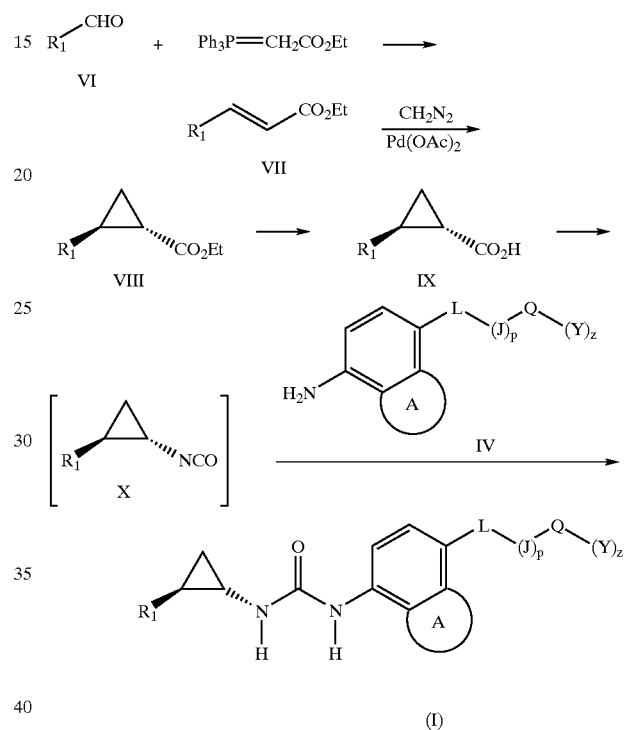

wherein n is 1, and the cyclopropyl group has the stereochemistry shown above;

said process comprising
   reacting the aldehyde bearing $R_1$ or $R_2$ (VI) with the carbethoxymethylene triphenylphosphorane in a suitable solvent to provide the alpha, beta-unsaturated ester (VII);
   reacting compound (VII) with diazomethane in the presence of palladium (II) acetate in a suitable solvent at a temperature of about 0° C. to room temperature to provide the cyclopropane carboxylic acid ester (VIII);
   hydrolyzing the ester (VIII) under suitable conditions to provide the carboxylic acid (IX) compound;
   reacting carboxylic acid compound (IX) under suitable conditions for converting via Curtius rearrangement to provide the isocyanate (X);
   reacting the isocyante (X) with the intermediate (IV) to provide compounds of the formula (I) with the stereochemistry indicated in the formula (I) shown above and subsequently isolating the product compound.

* * * * *